US012577274B2

(12) United States Patent　　(10) Patent No.: US 12,577,274 B2
Eisenhuth et al.　　(45) Date of Patent:　Mar. 17, 2026

(54) MANUFACTURE OF GLUCAGON PEPTIDES

(71) Applicant: BACHEM HOLDING AG, Bubendorf (CH)

(72) Inventors: Ralf Eisenhuth, Basel (CH); Guenther Loidl, Rheinfelden (DE); Daniel Samson, Basel (CH); Ralph O. Schoenleber, Lupsingen (CH)

(73) Assignee: BACHEM HOLDING AG, Bubendorf (CH)

( * ) Notice: Subject to any disclaimer, the term of this patent is extended or adjusted under 35 U.S.C. 154(b) by 1105 days.

(21) Appl. No.: 16/962,793

(22) PCT Filed: Jan. 30, 2019

(86) PCT No.: PCT/EP2019/052183
§ 371 (c)(1),
(2) Date: Jul. 16, 2020

(87) PCT Pub. No.: WO2019/149723
PCT Pub. Date: Aug. 8, 2019

(65) Prior Publication Data
US 2021/0122782 A1　Apr. 29, 2021

(30) Foreign Application Priority Data
Jan. 30, 2018　(EP) ..................................... 18154113

(51) Int. Cl.
*C07K 1/20*　(2006.01)
*C07K 1/18*　(2006.01)
*C07K 14/605*　(2006.01)

(52) U.S. Cl.
CPC .................. *C07K 1/20* (2013.01); *C07K 1/18* (2013.01); *C07K 14/605* (2013.01)

(58) Field of Classification Search
CPC ........... C07K 1/20; C07K 1/18; C07K 14/605
See application file for complete search history.

(56) References Cited

U.S. PATENT DOCUMENTS

| 4,033,941 | A | 7/1977 | Stilz et al. |
| 2010/0087654 | A1 | 4/2010 | Hildbrand |
(Continued)

FOREIGN PATENT DOCUMENTS

| CN | 103333239 | * 10/2013 |
| CN | 103333239 A | 10/2013 |
(Continued)

OTHER PUBLICATIONS

Welinder, Benny S. et al. "Use of polymeric reversed-phase cols. for the characterization of polypeptides extracted from human pancreata: I. Effect of the mobile phase." Journal of Chromatography A 542 (1991): 65-81 (Year: 1991).*
(Continued)

*Primary Examiner* — Louise W Humphrey
*Assistant Examiner* — Mary A Crum
(74) *Attorney, Agent, or Firm* — RAPHAEL BELLUM PLLC

(57) ABSTRACT

The present invention refers to a method of purifying a glucagon peptide, the method comprising a two dimensional reversed phase high performance liquid chromatography protocol, wherein the first step is carried out at using a mobile phase comprising a triethylammonium phosphate (TEAP) buffer and acetonitrile, and the second step is carried out at using a mobile phase comprising aqueous acetic acid and acetonitrile.

21 Claims, 3 Drawing Sheets

Specification includes a Sequence Listing.

(56)                    References Cited

U.S. PATENT DOCUMENTS

| 2017/0313740 | A1 | | 11/2017 | Wang et al. |
| 2020/0399339 | A1 | | 12/2020 | Orlandin et al. |

FOREIGN PATENT DOCUMENTS

| CN | 103694338 | A | | 4/2014 | |
| CN | 103333239 | B | * | 6/2015 | |
| EP | 3753946 | A1 | | 12/2020 | |
| JP | 2008509221 | A | | 3/2008 | |
| JP | 2009510057 | A | | 3/2009 | |
| JP | 2010531828 | A | | 9/2010 | |
| JP | 2012504154 | A | | 2/2012 | |
| JP | 2012511902 | A | | 5/2012 | |
| JP | 2014210783 | A | | 11/2014 | |
| KR | 0149955 | B1 | | 3/1999 | |
| WO | 2004/089504 | A1 | | 10/2004 | |
| WO | 2005019262 | A1 | | 3/2005 | |
| WO | 2006020491 | A1 | | 2/2006 | |
| WO | 2007040711 | A2 | | 4/2007 | |
| WO | 2009003666 | A1 | | 1/2009 | |
| WO | 2010/040660 | A1 | | 4/2010 | |
| WO | 2010070255 | A1 | | 6/2010 | |
| WO | WO-2011050174 | A1 | * | 4/2011 | ............... A61P 1/00 |
| WO | WO-2016005960 | | * | 1/2016 | |
| WO | 2017/162650 | A1 | | 9/2017 | |
| WO | 2017/162653 | A1 | | 9/2017 | |
| WO | 2020254479 | A1 | | 12/2020 | |

OTHER PUBLICATIONS

Carr, David. "The handbook of analysis and purification of peptides and proteins by reversed-phase HPLC." Hesperia, CA, USA: Grace Vydac (2002): 1-14 (Year: 2002).*
Goncalves, Victor, et al. "Total chemical synthesis of the D2 domain of human VEGF receptor 1." Journal of Peptide Science: An Official Publication of the European Peptide Society 15.6 (2009): 417-422 (Year: 2009).*
Subiros-Funosas, et al. "Oxyma: An Efficient Additive for Peptide Synthesis to Replace the Benzotriazole-Based HOBt and HOAt with a Lower Risk of Explosion [1]." Chemistry—A European Journal 15.37 (2009): 9394-9403 (Year: 2009).*
Huang, H., and D. L. Rabenstein. "A cleavage cocktail for methionine-containing peptides." The Journal of peptide research 53.5 (1999): 548-553 (Year: 1999).*
Mojsov, Svetlana, and R. B. Merrifield. "Solid-phase synthesis of crystalline glucagon." Biochemistry 20.10 (1981): 2950-2956 (Year: 1981).*
Fourmy, et al. "Separation of the Secretin-Glucagon Family Peptides by RP-HPLC in Triethylammonium Phosphate Buffers." Journal of Liquid Chromatography 5.11 (1982): 2123-2134 (Year: 1982).*
Berks, et al. "Isolation and structural characterization of insulin and glucagon from the holocephalan species *Callorhynchus milii* (elephantfish)." Biochemical Journal 263.1 (1989): 261-266 (Year: 1989).*
Sigma, The Applications Book, Eliminate TFA and Improve Sensitivity of Peptide Analyses by LC/MS, Sep. 2002 (Year: 2002).*
Cardoso, et al. "The serendipitous origin of chordate secretin peptide family members." BMC evolutionary biology 10 (2010): 1-19 (Year: 2010).*
Anaspec, Glucagon (1-29), bovine, human, rat, porcine, anaspec.com/en/catalog/glucagon-1-29-bovine-human-rat-porcine~2b1ff873-f16e-4ed3-a1be-668bb5cdf8e0, 2025 (Year: 2025).*
Appendix A, sequence alignment SEQ ID No. 1 and porcine glucagon, 2025 (Year: 2025).*
Chabenne, Joseph R., et al. "Optimization of the native glucagon sequence for medicinal purposes." (2010): 1322-1331. (Year: 2010).*
Riester, Daniel, et al. "Racemization of amino acids in solid-phase peptide synthesis investigated by capillary electrophoresis." Analytical chemistry 68.14 (1996): 2361-2365 (Year: 1996).*
International Preliminary Report on Patentability in International Application No. PCT/EP2019/052183, dated Aug. 13, 2020.
Beaven et al., European J. Biochem. 11:37-42 (1969).
Yoshida and Terakoka, Annual Report of Shionogi Research Laboratories No. 48, 1-18 (1998).
Ishizaki et al., Appl Microbiol Biotechnol 36:483-486 (1992).
Mollerup et al., Book of Abstracts, 211th ACS National Meeting, New Orleans, LA, Mar. 24-28, 1996.
Wang et al., Mol. Pharmaceutics 12:411-419 (2015).
Gao et al., China Biotechnology, 2016, 36(12):15-20 (in Chinese with English abstract).
Newswanger et al., Journal of Diabetes Science and Technology, 2015, 9(1):24-33.

* cited by examiner

SEQUENCE LISTING

<160> NUMBER OF SEQ ID NOS: 6

<210> SEQ ID NO 1
<211> LENGTH: 29
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 28
<212> TYPE: PRT
<213> ORGANISM: Artificial Sequence
<220> FEATURE:
<223> OTHER INFORMATION: impurity of human glucacon - des-Thr5-glucagon

<400> SEQUENCE: 2

His Ser Gln Gly Phe Thr Ser Asp Tyr Ser Lys Tyr Leu Asp Ser Arg
1               5                   10                  15

Arg Ala Gln Asp Phe Val Gln Trp Leu Met Asn Thr
            20                  25

<210> SEQ ID NO 3
<211> LENGTH: 28
<212> TYPE: PRT
<213> ORGANISM: Artificial Sequence
<220> FEATURE:
<223> OTHER INFORMATION: impurity of human glucacon - des-Ser2-glucagon

<400> SEQUENCE: 3

His Gln Gly Thr Phe Thr Ser Asp Tyr Ser Lys Tyr Leu Asp Ser Arg
1               5                   10                  15

Arg Ala Gln Asp Phe Val Gln Trp Leu Met Asn Thr
            20                  25

<210> SEQ ID NO 4
<211> LENGTH: 29
<212> TYPE: PRT
<213> ORGANISM: Artificial Sequence
<220> FEATURE:
<223> OTHER INFORMATION: impurity of human glucacon - Glu24-glucagon

<400> SEQUENCE: 4

His Ser Gln Gly Thr Phe Thr Ser Asp Tyr Ser Lys Tyr Leu Asp Ser
1               5                   10                  15

Arg Arg Ala Gln Asp Phe Val Glu Trp Leu Met Asn Thr
            20                  25

<210> SEQ ID NO 5
<211> LENGTH: 4
<212> TYPE: PRT
<213> ORGANISM: Artificial Sequence
<220> FEATURE:
<223> OTHER INFORMATION: example peptide to indicate nomenclature

<400> SEQUENCE: 5

Gly Leu Ala Phe
1

<210> SEQ ID NO 6

-continued

```
<211> LENGTH: 5
<212> TYPE: PRT
<213> ORGANISM: Artificial Sequence
<220> FEATURE:
<223> OTHER INFORMATION: example peptide indicating nomenclatide of
      amino acid moiety positions

<400> SEQUENCE: 6

Gly Leu Ala Phe Ala
1               5
```

MANUFACTURE OF GLUCAGON PEPTIDES

SEQUENCE LISTING

The Sequence Listing, submitted herewith via EFS-Web, is an ASCII text file (2020-07-16_Sequence_listing_ST25.text, created on Jul. 16, 2020, 2128 bytes) is hereby incorporated by reference.

The present invention generally relates to the field of peptide manufacture at an industrial or laboratory scale. The present invention is directed to methods of effectively synthesizing and purifying a glucagon peptide.

Human glucagon is a product of the GCG gene (HGNC: 4191). The peptide has an average molecular mass of 3482.80 g/mol and consists of the following sequence of 29 amino acids, written in one-letter code:

(SEQ ID NO: 1)
HSQGTFTSDYSKYLDSRRAQDFVQWLMNT

Endocrine glucagon is produced by alpha cells of the pancreas and is a central catabolic hormone.

Glucagon is used as a medication, inter alia as an emergency treatment of severe hypoglycemia. Glucagon for therapeutic purposes was initially extracted and purified from bovine and porcine pancreas. Nowadays, glucagon is produced at an industrial scale mostly by recombinant techniques and—more recently—also by chemical peptide synthesis.

Chemical peptide synthesis has been extensively described in the literature. Two standard approaches to chemical peptide synthesis can be distinguished, namely liquid phase peptide synthesis (LPPS) and solid phase peptide synthesis (SPPS). Moreover, hybrid approaches can be utilized, where fragments are first synthesized by one of the above techniques and then joined together using the other. LPPS, also referred to as solution phase peptide synthesis, takes place in a homogenous reaction medium. Successive couplings yield the desired peptide. In SPPS, a peptide anchored to an insoluble polymer resin is assembled by the successive addition of the protected amino acids constituting its sequence. Most commonly, the peptide is anchored via its C-terminal amino acid and synthesis proceeds from the C-terminus to the N-terminus.

Because the growing chain is bound to the insoluble support, the excess of reagents and soluble by-products can be removed by simple filtration. However, in particular for the synthesis of large peptides, resin-bound side products can accumulate during each cycle of peptide chain elongation. As a result, the purification of the final product may be very challenging.

Purification of glucagon peptides is particularly demanding due to their propensity to aggregate. It is known that glucagon tends to aggregate at acidic pH (e.g. European J. Biochem. 11 (1969) 37-42). The present invention provides methods for the production and purification of glucagon peptides.

In spite of its long history as a therapeutic, the literature on glucagon preparation and purification is limited.

U.S. Pat. No. 4,033,941 discloses a method of enriching glucagon from a natural source. The method relies on repeated size exclusion chromatography using a feed solution and mobile phase having a pH of from about 9 to about 11. It is taught to avoid purification steps at acidic pH, because glucagon tends to form gels and fibrils in acidic solution.

Patent KR-B 0149955 reports the recombinant expression of a glucagon tumor necrosis factor fusion protein in *E. coli*. The fusion protein is cleaved and glucagon purified by HPLC using a C18 stationary phase. No details on the purification are given.

Yoshida and Terakoka (Annual Report of Shionogi Research Laboratories No 45, 1-18, 1998) teach the purification of recombinant glucagon as a fusion protein with human interferon gamma. Glucagon is retrieved from inclusion bodies by solubilization and cleavage of the fusion protein. Various purification protocols are disclosed. A two-step protocol using C18 reverse phase HPLC followed by ion-exchange DEAE-HPLC is reported to give unsatisfactory yields. Improved protocols involve an S-Sepharose chromatography step, followed by desalting using a Sephadex G-15 column and size exclusion chromatography using a Sephacryl-S100 column. Most preferred for large scale production was a purification scheme relying on differential isoelectric precipitation.

Ishizaki et al. (Appl Microbiol Biotechnol (1992) 36:483-486) describe the purification of large amounts of recombinant glucagon. A recombinantly expressed glucagon fusion protein is isolated from inclusion bodies, is cleaved with a specific protease, and the cleavage product is purified by C18 reverse-phase HPLC employing a linear gradient of 32-42% acetonitrile in 0.1 trifluoroacetic acid. The glucagon peptide containing fraction had a purity of about 90% and was subsequently purified by ion-exchange HPLC using a linear gradient of 0-0.1M NaCl in 10 mM TRIS-HCl, pH 8.5, 20% acetonitrile. The purity of the end-product is not disclosed.

Mollerup et al (Book of Abstracts, 211th ACS National Meeting, New Orleans, LA, Mar. 24-28, 1996) teach another method for the production of recombinant glucagon. Glucagon is expressed in *S. cerevisiae* and purified in a series of chromatographic steps.

The above methods have been optimized for the purification of recombinantly expressed glucagon after solubilisation from inclusion bodies and protease cleavage. It should be noted that such samples are of lower complexity than those resulting from chemical peptide synthesis, in particular from SPPS.

Patent application CN-A 103333239 discloses Fmoc SPPS of glucagon, wherein the coupling is performed at high temperatures. Optionally, a pseuoproline dipeptide is used.

Patent application CN-A 103694338 describes the purification of a crude glucagon preparation obtained by SPPS (cf. examples 1-3). The crude peptide is dissolved in 30% acetic acid and 5% aqueous acetonitrile, filtered, diluted and purified by a three-step procedure. First, reversed-phase chromatography is carried out using octadecyl silane bonded silica as the stationary phase and an acetonitrile gradient in a mobile phase comprising aqueous sulfuric acid and perchloric acid. The second step comprises salting out after adjusting the pH with ammonia. The precipitate is then redissolved in aqueous perchloric acid. In the third step, anion exchange is performed. The dissolved precipitate of step two is loaded on C18 stationary phase, washed with a mobile phase comprising acetonitrile and ammonium acetate in aqueous solution, and eluted with an aqueous solution comprising hydrochloric acid.

The method is said to give good yields and a purity above 99.0%. However, the impurity profile of the glucagon thus prepared is not disclosed. Moreover, perchloric acid is dangerously corrosive, readily forms potentially explosive mixtures, and is subject to extensive regulations. For the sake of process and product safety, it is therefore desirable to avoid the use of perchloric acid.

There is still a need for improved methods enabling the industrial production of highly pure glucagon. In particular, an economically viable method of glucagon purification is required, which allows the removal of related substances such as des-Thr5-, des-Ser2, and Glu24-glucagon, while avoiding peptide aggregation.

Surprisingly, a simple method for the preparation of highly pure glucagon has been found. It has been found advantageous to employ two consecutive chromatographic steps using hydrocarbon bonded silica as a stationary phase and a first mobile phase comprising triethylammonium phosphate and acetonitrile in a first step, followed by a second step with a second mobile phase comprising aqueous acetic acid and acetonitrile. Surprisingly, both purification steps were found to be complementary in their purification pattern. In the experiments performed, reproducibly high yields and high purities of the pooled fractions above 99.0% and even 99.3% could be achieved and gelling of the obtained product was well controlled.

In general, several abbreviations and definitions are used throughout the present invention:

Å Ångström (0.1 nm)
ACN acetonitrile
AcOH acetic acid
Boc tert. butyloxycarbonyl
DBU diazabicyclo[5.4.0]undec-7-ene
DEPBT 3-(diethoxy-phosphoryloxy)-3H-benzo[d][1,2,3] triazin-4-one
DIC diisopropylcarbodiimide
DIPEA diisopropylethylamine
Dmb 2,4-dimethoxybenzyl
DMF N,N-dimethylformamid
DTE 1,4-dithioerythriol
DTT 1,4-dithiothreitol
EDT 1,2-ethanedithiol
Fmoc 9-fluorenylmethyloxycarbonyl
GLP-1 glucagon-like peptide 1
GLP glucagon-like peptide
HOBt hydroxybenotriazole
HPLC high performance liquid chromatography
    The term HPLC as used herein includes UHPLC.
IPE diisopropyl ether
LC-MS Liquid chromatography-mass spectrometry
LOD Limit of detection
LPPS liquid phase peptide synthesis
MTBE methyl tert. butyl ether
MTT 4-methyltrityl
NH₄OAc ammonium acetate
NMP N-methylpyrrolidone
OMpe 3-methylpent-3-yl ester
OtBu tert. butyl ester
ONSu N-hydroxysuccinimide (also known as (aka.) OSu)
Oxyma cyano-hydroxyimino-acetic acid ethyl ester (aka. OxymaPure®)
Pbf 2,2,4,6,7-Pentamethyldihydrobenzofurane-5-sulfonyl
RP-HPLC reversed phase high performance liquid chromatography
RT room temperature
SEC size exclusion chromatography
SPPS solid-phase peptide synthesis
tBu tert. Butyl
TBTU (benzotriazolyl)tetramethyluronium tetrafluoroborate
TEAP triethylammonium phosphate
TES triethylsilane TFA trifluoroacetic acid
THF tetrahydrofuran
TIPS=TIS triisopropylsilane
Trt trityl
UHPLC ultra high performance liquid chromatography Unless indicated otherwise, liquid mixtures are defined by volume percentages and volume ratios at ambient temperature.

Unless otherwise stated, pH values are indicated for the temperature at which the respective aqueous solution is to be used. By definition, a pH value can only be indicated for an aqueous solution, e.g. for the aqueous component used in preparing a mobile phase.

As used in the context of the present application, the term "about" is used to indicate deviations of up to 10% from any given numerical value.

As used in the context of the present application, expressions like "composition C" or "composition GC" may be understood as synonymous with "composition (C)" or composition (GC)", i.e. "C" and "GC" may be understood as a reference mark.

The term "protecting group" as used herein may be understood in the broadest sense as a group which is introduced into a molecule by chemical modification of a functional group to block said group from reaction in subsequent process steps, e.g. to prevent side reactions of the amino acid side chains. Examples of amino protecting groups are the Boc and Fmoc groups, examples of carboxylic acid protecting groups are unreactive esters such as methyl esters, benzyl esters, or tert. butyl esters.

Amino acids will be referred to interchangeably by either their full name (exemplified: alanine), 3-letter code according to WIPO Standard ST. 25 (e.g. Ala), or 1-letter code (e.g. A). As far as the enantiomeric form is not expressly specified, L-amino acids are in general referred to. It should be noted, however, that the present invention can likewise be put to practice using D-amino acids and other stereoisomers.

As used herein, the term "peptide" and "polypeptide" may be understood interchangeably. It refers to polymers of two or more amino acids, which are linked by peptide bonds. In the case of alpha amino acids, the peptide bonds may be amide bonds between the alpha carboxyl group of one amino acid and the alpha amino group of the following amino acid. It should be noted that the term "peptide" or "polypeptide" includes branched and circular peptides, peptides comprising non-natural amino acids, isotope labeled peptide versions, and peptide derivatives. Branched peptides may result, e.g., from linking two peptide chains via amino acid side chains, either directly or via a molecular linker. Circular peptides may result, e.g., from intramolecular disulfide bond formation, or from intramolecular condensation reactions between functional groups at the termini or amino acid side chains.

Peptide derivatives include, e.g., peptides with acylated, acetylated, amidated, and/or otherwise modified functional groups at the termini or amino acid side chains.

Unless indicated otherwise, peptide sequences are indicated herein starting with the N-terminus (left) and ending with the C-terminus (right). Table 1 illustrates different notations, which are equivalent and will be used interchangeably throughout this document.

5

TABLE 1

Notation of peptides

| Notation of an example peptide of SEQ ID NO: 5 | Explanation |
|---|---|
| H-Gly-Leu-Ala-Phe-OH | This notation stresses that the N-terminal amino group ("H") and C-terminal carboxyl ("OH") group are not modified. |
| Gly-Leu-Ala-Phe | Terminal groups are only expressly stated if they are modified. |
| GLAF | 1-letter code. Terminal groups are only expressly stated if they are modified. |
| Glycyl-L-leucyl-L-alanyl-L-phenylalanine | "written out in full" |

Specific amino acids within a peptide sequence are referred to herein by indicating the position number in Arabic numbers, optionally in superscript. As an example, the amino acid Ala (aka. A) in position 3 of peptide Gly-Leu-Ala-Phe-Ala (SEQ ID NO: 6) aka. GLAFA) would be referred to as Ala3 or $Ala^3$ or A3 or $A^3$. These notations are used interchangeably.

The following notation will be used for amino acid derivatives: Substituents at the alpha amino group (Nα) are indicated to the left of the amino acid symbol and separated by a hyphen, substituents at the alpha carboxy group are indicated to the right of the amino acid symbol and separated by a hyphen, substituents at the side chain are indicated in brackets immediately to the right of the amino acid symbol. Substituents at the sided chain of His are usually located at the nitrogen atom in position 1 of the imidazole ring. The substituent's position is often not explicitly specified. Therefore, e.g. Fmoc-His(Trt)-OH encompasses in particular Fmoc-His(1-Trt)-OH. For unmodified alpha-amino acids, the substituent at the alpha amino group (Nα) is a proton (H—) and the substituent at the alpha carboxy group is a hydroxyl (—OH). The analogous notation is used for substituted amino acids, which are part of a peptide.

The term "analogs" or "analogs" as used herein is used for peptides whose sequence is derived from a first peptide sequence by replacement of up to three amino acid moieties, and/or by deletion of up to three amino acid moieties of said first peptide sequence, and/or by addition of up to three amino acid moieties.

The term "derivative" or "derivatives" as used herein refers to a compound which can be obtained from a first compound by a chemical reaction. As a result, a derivative may differ from the first compound by the presence or absence of substituents. For example, amino acid derivatives for use in SPPS usually differ from the amino acid they are derived from at least by the presence of an amino protecting group. Peptide derivatives include in particular acylated, amidated, pegylated and otherwise labeled versions of the peptide.

The term "glucagon-like peptide" or GLP as used herein refers to the homologous peptides derived from the GCG gene (HGNC: 4191), the exendins and analogs thereof as well as derivatives of any of the foregoing.

The terms "glucagon-like peptide 1 analogs" and "GLP-1 analogs" are used herein interchangeably. As used herein, they relate to peptides capable of binding to the GLP-1 receptor. Derivatives and analogs of GLP-1 (7-37) and of exendins 4 (1-39) such as Exenatide, Lixisenatide, Semaglutide and Liraglutide are preferred GLP-1 analogs.

As used herein, the expressions "glucagon" and "a glucagon peptide" are used interchangeably to refer to a peptide of SEQ ID NO: 1 (His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr), or a derivative or an analog thereof.

In a particularly preferred embodiment, the glucagon peptide (intended to be prepared according to the method of the present invention) is a peptide of SEQ ID NO: 1.

Alternatively, glucagon peptides of the present invention may also be peptides, which differ from SEQ ID NO: 1 by addition, insertion, deletion and/or substitution of up to three amino acids. This means that up to three amino acid positions may be considered as differing—be it due to addition, insertion, deletion, and/or substitution of amino acid residues—from SEQ ID NO: 1 based on a sequence alignment of the peptide in question with the peptide of SEQ ID NO: 1. Typical sequence alignment tools such as BLAST or ClustalW are well known to the person skilled in the art. Such glucagon peptide that include an addition, an insertion, a deletion and/or a substitution of up to three amino acids are preferably included in crude glucagon peptide mixtures that also comprise the glucagon peptide of interest (i. particular the glucagon peptide of SEQ ID NO: 1). However, it will be understood that such glucagon peptide that includes an addition, an insertion, a deletion and/or a substitution of up to three amino acids may, alternatively, also be the glucagon peptide of interest. Therefore, such glucagon peptide that includes an addition, an insertion, a deletion and/or a substitution of up to three amino acids may optionally also be the glucagon peptide to be prepared (and purified). Then, retention times will be different. The person skilled in the art will adapt the conditions accordingly.

As used herein, sequence homology may refer to any definition of sequence homology known in the art. In particular, sequence homology may be understood as sequence homology determined by BLAST (Basic Local Alignment Search Tool) of the National Center for Biotechnology Information (NCBI) in the version of the filing date of the present application.

Preferably, the glucagon peptide (in soluble form, i.e., once cleaved off its resin) is (essentially) free of any protecting groups and has no modifications at amino acid side chains. Accordingly, the glucagon peptide is preferably the fully unprotected peptide, which is preferably not further modified.

Alternatively, the N-terminus of the glucagon peptide may be modified (e.g, acylated, in particular acetylated). Alternatively or additionally, the C-terminus may be modified (e.g., amidated).

Alternatively or additionally, one or more amino acid moiety side chains may be conjugated with a fluorophore. Optionally, the glucagon peptide may also be labeled radioactively (e.g., by 3H, 32P, 35S, 14C, 99mTc or lanthanides (e.g., 64Gd)) or may be labelled with a spin label, such as one or more heavy isotopes, e.g., 13C, detectable by Nuclear Magnetic Resonance (NMR).

The glucagon peptide will typically consist of natural L-amino acids. However, alternatively, the peptide may also comprise one or more non-natural amino acid(s) such as, e.g., D-amino acid(s), beta amino acid(s), methylated amino acid(s) (e.g., N-methylated or alpha-methylated amino acid(s)) or may even consist of such.

The person skilled in the art will notice that in a polar environment, in particular in an aqueous environment, the peptide strand of the glucagon peptide may form a salt such as, e.g., by means of binding protons or other cations and/or anions, releasing protons or other cations and/or anions at the termini and/or a some of the amino acid side chains.

It will be understood by a person skilled in the art that a glucagon peptide as used herein may optionally bear any counter ions known in the art, such as anions or cations, such as e.g., chloride ions, acetate ions, carbonate ions, hydrocarbonate ions, sodium ions, potassium ions, magnesium ions, any ions of a cleavage solution (e.g., TFA ions, bromide ions, perchlorate ions, ammonium ions) and/or cations or anions of residuals of protecting groups. Further, a peptide may optionally be covalently or non-covalently associated to traces of one or more scavengers, such as, e.g., triisopropylsilane (TIS), dithiothreitol (DTT), anisole, thioanisole or 1,2-ethanedithiol.

The present invention is directed to methods for effectively synthesizing and purifying a glucagon peptide.

In particular, one aspect of the present invention relates to a method for the preparation of a glucagon peptide, comprising:

a) Providing a liquid composition C comprising a glucagon peptide and at least one unwanted component;

b) Subjecting the composition C to a first reversed phase high performance liquid chromatography (RP-HPLC) purification, wherein a hydrocarbon bonded silica is used as a stationary phase, an aqueous mobile phase comprising triethylammonium phosphate and acetonitrile is used, and elution is effected by gradually increasing the acetonitrile concentration within the mobile phase while collecting fractions containing the glucagon peptide; and c) Subjecting the pooled glucagon peptide containing fractions obtained in step b) to a second reversed phase HPLC purification, wherein a hydrocarbon bonded silica is used as a stationary phase, a mobile phase comprising acetic acid and acetonitrile is used, and elution is effected by gradually increasing the acetonitrile concentration within the mobile phase while collecting fractions containing the purified glucagon peptide.

In one embodiment, the method of the present invention further comprises the step of d) Performing an anion exchange, preferably wherein acetate is replaced by chloride and/or wherein the anion exchange is achieved by lyophilization, ultrafiltration, dialysis, solid phase extraction, reversed-phase chromatography or by ion exchange chromatography.

The term "providing a liquid composition C comprising glucagon and at least one unwanted component" may be understood in the broadest sense as obtaining any liquid composition containing glucagon and at least one unwanted component. Glucagon may be provided by any means known in the art. Exemplarily, it may be obtained from a biotechnological method, from Solid Phase Peptide Synthesis (SPPS) or Liquid Phase Peptide Synthesis (LPPS) or a combination thereof. The liquid composition C may essentially comprise a crude glucagon peptide or may comprise a partially purified glucagon peptide.

In a preferred embodiment of the invention, step a) comprises the steps of:

(a-i) providing a glucagon peptide conjugated to a solid phase, wherein at least the side chains of Glu, Asp, and Lys carry protecting groups; and (a-ii) cleaving the glucagon peptide from the solid phase and, preferably, removing the protection groups from the glucagon peptide.

For the purpose of the present application, the terms "raw" and "crude" are used interchangeably to designate preparations of a peptide such as glucagon, which are essentially a direct product of synthesis and isolation processes and have not yet been submitted to specific purification steps such as chromatography. Chemical synthesis usually yields crude glucagon preparations having a purity of around 40 to 70%. It should however be understood that the liquid composition C may be characterized by any degree of purity below 100% (e.g. a purity above 30, 40, 50, 60, 70, 80, 90, or 95%) and that the embodiments of the present invention may also be advantageously applied to partially purified glucagon compositions.

The term "the pooled glucagon containing fractions obtained in step b" may be understood to relate to a pool of glucagon containing fractions of suitable purity obtained in step b. Selection of the fractions to be pooled, i.e. combined, for further processing may be based on analysis of the glucagon content and purity in the fractions obtained.

The term "unwanted component" is used herein in the broadest sense for any compound considered an impurity. Particularly preferred types of impurities are formed during synthesis and storage of glucagon and may exemplarily be selected from the group consisting of amino acids, peptides and derivatives thereof. In particular encompassed are impurities selected from the group consisting of amino acids, peptides, and derivatives thereof, which may result from processes such as premature chain termination during peptide synthesis, omission or unintended addition of at least one amino acid during peptide synthesis, incomplete removal of protecting groups, side reactions occurring during amino acid coupling or Fmoc deprotection steps, interor intramolecular condensation reactions, side reactions during peptide cleavage from a solid support, racemization, any other type of isomer formation, deamidation, (partial) hydrolysis, and aggregate formation. It is well known in the art that glucagon is prone to aggregate formation, and that low pH values often facilitate this process, i.e. that low pH values represent a destabilizing condition (cf., e.g., Wang et al., Mol. Pharm 12:411-419). Peptidic contaminations resulting from such processes as outlined above are sometimes referred to as "related substances".

In a particularly preferred embodiment, the unwanted component is a peptidic impurity. As used herein, the expression "peptidic impurity" refers to unwanted peptidic compounds and comprises in particular HMW (High Molecular Weight) impurities, derivatives of the peptide to be purified, truncated variants of the peptide to be purified, deletion variants of the peptide to be purified, and derivatives of such truncated and deletion variants. Peptidic impurities are routinely determined by suitable analytic chromatography methods including RP-UHPLC.

In one embodiment, the unwanted component comprises covalent or non-covalent aggregates of the glucagon peptide to be purified. Such unwanted components are physiologically inactive or of unknown physiological effect and have a molecular weight above 5000 Da. They are referred to herein as "high molecular weight (HMW) impurities". In another embodiment, the unwanted component is a derivative of the peptide to be purified, e.g. the result of amino acid racemization, oxidation or hydrolysis of amino acid side chains, and/or a side product formed during peptide synthesis. In another embodiment, the unwanted component is a truncated variant of the peptide to be purified or a derivative of such a truncated variant. As used herein, the expression "truncated variant" refers to continuous fragments, i.e. subsequences without gaps, of a given peptide, which lack one or more amino acids at the N-terminus and/or the C-terminus of the peptide sequence. In another preferred embodiment, the unwanted component comprises deletion variants of the peptide to be purified or derivatives of such deletion variants. As used herein, the expression "deletion variant" is used to refer to variants of the peptide to be purified, which differ from it in that their primary sequence lacks a single or multiple amino acid(s). The "omitted" amino acid(s) may be at any position within the original peptide sequence. Hence, truncation variants can be considered a specific type of deletion variants.

In a most preferred embodiment, the method according to the present invention allows to remove peptidic impurities so as to yield an essentially pure glucagon preparation. It was shown that the methods of the present invention yield essentially pure glucagon peptide containing not more than 0.5% of any individual peptidic impurity, as assessed in terms of relative peak area observed by analytical chromatography, preferably with UV detection at a wavelength between 205 and 230 nm.

In some embodiments, the unwanted component comprises at least one species of Met(O)$^{27}$-glucagon, and/or a glucagon deletion variant lacking Ser$^2$ or Thr$^5$ and/or Glu$^{24}$-glucagon.

In one embodiment, the unwanted component comprises des-Thr$^5$-glucagon (SEQ ID No: 2), des-Ser$^2$-glucagon (SEQ ID No: 3), and/or Glu$^{24}$ glucagon (SEQ ID No: 4).

The embodiments of the invention described herein can advantageously be used to purify glucagon from a crude preparation obtained after synthesis. Although the present invention is in no way limited to specific methods of glucagon synthesis, a preferred embodiment involves the purification of a chemically synthesized glucagon peptide. The glucagon peptide may be synthesized, e.g., by Fmoc solid-phase peptide synthesis using suitably protected amino acid and dipeptide derivatives.

Preferably, the composition C comprises a glucagon peptide or a salt thereof, which was prepared by a method comprising the following steps (a-i)-(a-iii):

(a-i) Solid phase synthesis of a glucagon peptide;

(a-ii) Cleavage of the glucagon peptide from the solid phase and, preferably, removing the protection groups from the glucagon peptide; and (a-iii) Separation of the glucagon peptide from the components of the cleavage solution Consequently, in one embodiment, step a) of the method according to the present invention may comprise performing steps (a-i), (a-ii), and (a-iii) above.

The terms "solid phase", "resin", "[resin]", and "support" are used exchangeably herein. They may be understood in the broadest sense as any structure, e.g. a bead-like structure, usable for SPPS.

SPPS is commonly carried out on gel phase rather than solid phase supports. Suitable resins may be based on polystyrene, polystyrene-PEG composites, PEG, PEGA, cross-linked ethoxylate acrylate (CLEAR), polyamides, polydimethylacrylamide, or any other support with the desired physical and chemical properties. Resins based on beaded polystyrene with 1% divinylbenzene are among the routinely used supports, typically having a size distribution of 200-400 mesh or 100-200 mesh. Polystyrene based 2-Chlorotrityl chloride (CTC) resin, diphenyldiazomethane (PDDM) resin, 4-(2',4'-Dimethoxyphenyl-Fmoc-aminomethyl)-phenoxymethyl-polystyrene (Rink) resin, 2-Methoxy-4-alkoxybenzyl alcohol (Sasrin) resin, and especially 4-Alkoxybenzyl alcohol (Wang) resin are particularly suitable for use with the methods of the present invention and are commercially available from suppliers such as Sigma-Aldrich, Bachem and EMD Millipore. However, any other resin suitable for SPPS may be used.

As an alternative to immobilization via the C-terminal carboxyl group, the peptide may also be conjugated to the resin via a side chain of a (preferably terminal) amino acid. As a further alternative, the peptide may also be conjugated to the resin via the N-terminus and synthesized from the N- to the C-terminus (inverse peptide synthesis).

The person skilled in the art will be aware of a large variety of SPPS methods. In general, any type of SPPS may be used in the context of the present invention. Various types of equipment can be used for SPPS. Manual, semi-automated and automated synthesizers for either batchwise or continuous flow SPPS are available. For any given equipment, the resin may be chosen properly so as to meet the mechanical requirements imposed by the equipment.

The person skilled in the art is well aware of the fact that resin load may influence effectivity in SPPS, in particular in industrial SPPS. This may have particular impact when dealing with long, aggregation-prone peptide sequences such as a glucagon peptide: On one side, process efficiency increases with increasing resin load. On the other side, it is essential to reduce on-resin precipitation by reducing resin load. Hence, a delicate balance may be met and the optimal resin load can be established by routine experimentation for any given SPPS protocol. Resin load can be varied, e.g., either by using resins for which different substitution degrees are commercially available, or by coupling the second amino acid in molar deficit relative to the first amino acid, and subsequently acetylating, i.e. blocking, unreacted first amino acids. Likewise, the first amino acid may be coupled in molar deficit to the resin, followed by a blocking step.

In preferred embodiments of the present invention, a resin load in the range of around 0.2 mmol/g to around 0.9 mmol/g is used, for example around 0.2 mmol/g, 0.3 mmol/g, 0.4 mmol/g, 0.5 mol/g, 0.6 mmol/g, 0.7 mmol/g, 0.8 mmol/g, or 0.9 mmol/g. In this context, it may be noted that, during SPPS, the swelling and shrinking of the resin in the various solvents used can lead to considerable fluctuations of resin volume and hence peptide concentration on the resin.

In a preferred embodiment of the present invention, Fmoc SPPS is performed. The person skilled in the art is well-aware of SPPS methods based on an Fmoc synthesis protocol. Each cycle of amino acid addition to the resin typically starts with Fmoc cleavage, i.e., removal of the Fmoc protecting group from the resin-bound peptide chain. This is achieved by incubating the peptide resin with a base in a solvent capable of swelling the resin and dissolving the reagents. Popular bases for this purpose comprise, e.g., secondary amines such as piperidine and 4-methyl piperidine. Suitable solvents comprise, e.g., DMF, NMP, dimethyl sulfoxide, dichloromethane, tetrahydrofuran, acetonitrile, toluene, and mixtures thereof. The reaction is commonly carried out at ambient temperature, e.g. within a temperature range of 15-30° C. Usually, the base-labile and acid-stable Fmoc is split off by a short treatment (2 to 15 minutes, e.g. 2, 3, 4, 5, 6, 7, 8, 9, 10, 11, 12, 13, 14, or 15 minutes) with 5-50%, preferably 20%, piperidine in DMF (v/v). Where necessary, this treatment is repeated and/or slightly prolonged (7 to 30 minutes, e.g. 7, 8, 9, 10, 11, 12, 13, 14, 15, 16, 17, 18, 19, 20, 21, 22, 23, 24, 25, 26, 27, 28, 29, or 30 minutes). For synthesis of large peptides with difficult-to-cleave stretches, the duration of Fmoc cleavage as well as the number of repetitions may be gradually increased. For instance, the cleavage time may be 15-75 minutes, e.g. 15, 30, 45, 60, or 75 minutes, and the cleavage may be repeated up to 8 times, e.g. 2, 3, 4, 5, 6, 7, or 8 times. Moreover, the temperature may be increased, e.g. to a temperature between 30° C. and 45° C. Under those conditions, complete deblocking is achieved in most cases. Additionally or alternatively, the reagent used for Fmoc cleavage may be varied.

It has been found that even slight variations of the reagent may considerably accelerate the cleavage, e.g. the use of: 1 to 5% DBU in DMF, 20% piperidine and 1-5% DBU in DMF, 20% piperidine in NMP, or 20% piperidine in DMF at 45° C. Moreover, acceleration of the cleavage reaction may be achieved by heating/microwave treatment.

On the other side, the nature of the peptide may render the use of milder treatments advantageous. Particular mild cleavage conditions are, e.g., 0.1 M HOBt plus 20% piperidine in DMF, 50% morpholine in DMF, 2% HOBt plus 2% hexamethyleneimine plus 25% N-methylpyrrolidine in 50% DMSO in NMP. The skilled person will routinely optimize and control Fmoc cleavage conditions at each step of the synthesis.

In a preferred embodiment, the Fmoc protecting group is cleaved off the growing peptide chain conjugated to the solid phase using a mixture selected from the group consisting of 5-50% (v/v) piperidine or 4-methyl piperidine in N,N-dimethylformamide (DMF), 5-50% (v/v) piperidine or 4-methyl piperidine in N-methylpyrrolidone (NMP), 1-5% (v/v) diazabicyclo[5.4.0]undec-7-ene (DBU) in DMF, and 50% (v/v) morpholine in DMF.

The cleavage reagent is typically washed out carefully after Fmoc-removal. DMF and optionally IPA are used for washing until neutral pH. To ensure complete base removal, it may be advantageous to add small amounts of HOBt in in later washing cycles.

The coupling of an amino acid derivative to the peptide resin, i.e. the elongation step, is one of the central steps of the SPPS cycle.

Suitable protected amino acid derivatives for Fmoc-SPPS, such as Fmoc-Ala-OH, Fmoc-Arg (Pbf)-OH, Fmoc-Arg (Pmc)-OH, Fmoc-Asn (Trt)-OH, Fmoc-Asn (Mtt)-OH, Fmoc-Asp(OtBu)-OH, Fmoc-Asp (OMpe)-OH, Fmoc-Cys (Trt)-OH, Fmoc-Cys (Mmt)-OH, Fmoc-Gly-OH, Fmoc-Gln (Mtt)-OH, Fmoc-Gln (Trt)-OH, Fmoc-Glu (OtBu)-OH, Fmoc-His(1-Trt)-OH, Boc-His(Trt)-OH (sometimes referred to as Boc-His(1-Trt)-OH), Boc-His(Boc)-OH (sometimes referred to as Boc-His(1-Boc)-OH), Fmoc-Ile-OH, Fmoc-Leu-OH, Fmoc-Lys (Boc)-OH, Fmoc-Met-OH, Fmoc-Phe-OH, Fmoc-Pro-OH, Fmoc-Ser (tBu)-OH, Fmoc-Thr(tBu)-OH, Fmoc-Trp (Boc)-OH, Fmoc-Tyr(tBu)-OH, and Fmoc-Val-OH, are commercially available from various sources. It should be noted that the use of non-natural amino acid derivatives such as Aib (α-aminoisobutyric acid), Nle (norleucine), or Orn (ornithine) in the synthesis of glucagon-like peptides is likewise encompassed by the methods of the present invention.

In a preferred embodiment, the amino acid derivatives Fmoc-Ala-OH, Fmoc-Arg (Pbf)-OH, Fmoc-Asn (Trt)-OH, Fmoc-Asp (OMpe)-OH, Fmoc-Gln (Trt)-OH, Fmoc-Gly-OH, Boc-His(Boc)-OH, Fmoc-Leu-OH, Fmoc-Lys (Boc)-OH, Fmoc-Met-OH, Fmoc-Phe-OH, Fmoc-Ser (tBu)-OH, Fmoc-Thr(tBu)-OH, Fmoc-Trp (Boc)-OH, Fmoc-Tyr(tBu)-OH, and Fmoc-Val-OH are used. In another preferred embodiment, the amino acid derivatives Fmoc-Ala-OH, Fmoc-Arg (Pbf)-OH, Fmoc-Asn (Trt)-OH, Fmoc-Asp (OMpe)-OH, Fmoc-Gln (Trt)-OH, Fmoc-Gly-OH, Boc-His (Trt)-OH, Fmoc-Leu-OH, Fmoc-Lys (Boc)-OH, Fmoc-Met-OH, Fmoc-Phe-OH, Fmoc-Ser (tBu)-OH, Fmoc-Thr(tBu)-OH, Fmoc-Trp (Boc)-OH, Fmoc-Tyr(tBu)-OH, and Fmoc-Val-OH are used.

Rate and yield of the coupling reaction may be influenced by various parameters such as the choice of solvent, the steric hindrance, and the reactivity of the activated carboxylic acid. The solvent may not only determine the swelling of the precursor peptide-resin and may thus influence the accessibility of the reactive sites; it may also directly affect the kinetics of the coupling reaction. Suitable solvents are capable of swelling the resin and dissolving the reagents and comprise, e.g., DMF, NMP, dimethyl sulfoxide, dichloromethane, tetrahydrofuran, acetonitrile, toluene, and mixtures thereof. The steric hindrance is determined by the nature of the amino acid side chains and their protecting groups. The reactivity of the activated carboxylic acid determines the acylation rate, as well as the extent of side reactions, such as racemization. Depending on the synthesis strategy chosen, peptide derivatives such as pseudoproline dipeptide derivatives, di- or tripeptide derivatives, or branched dipeptide derivatives may be used in lieu of single amino acid derivatives.

In certain embodiments of the present invention, amino acid activation is carried out in DMF as a solvent, i.e. the amino acid or peptide derivative, a coupling reagent and optionally an additive or base are dissolved in DMF and mixed. DIC may be used as coupling reagent in combination with either OxymaPure® or HOBt as an additive. In the alternative, TBTU or DEPBT may be used to convert the Fmoc amino acid into an active OBt or ODhbt ester in the presence of a base, preferably DIPEA.

As used herein, the term "coupling reagent mixture" relates to the composition comprising the coupling reagent and optionally an additive or a base. Preferred coupling reagent mixtures for use with the present invention comprise TBTU plus DIPEA, DIC plus Oxyma, DEPBT plus DIPEA, or DIC plus HOBt.

The amino acid derivative of choice is pre-activated by incubation with the above reagents for 1-30 min, e.g. for 2, 3, 4, 5, 6, 7, 8, 9, 10, . . . , 28, 29, or 30 min before addition to the resin. The coupling reaction is allowed to proceed for 1 to 74 h, e.g. for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, . . . , 71, 72, 73, or 74 h. The amino acid derivative may be used in a 0.4-3 molar ratio relative to the amount of resin-bound amine groups, e.g. at a molar ratio of 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0. In order to achieve complete coupling, it may be advantageous to add a second portion of activating agent or base to the reaction mixture after some time, e.g. after 10, 20, 30, 40, or 60 min. The pre-activation and coupling steps are commonly carried out at room temperature, but may also be performed at other temperatures. It may be advantageous to perform one or more re-coupling steps in order to achieve near to complete conversion of amino groups.

In other embodiments of the invention, amino acid activation is carried out in a solvent consisting of NMP, dimethyl sulfoxide, dichloromethane, tetrahydrofuran, acetonitrile, toluene, and mixtures thereof, optionally with DMF.

In one embodiment of the present invention, step a) comprises performing Fmoc-based solid phase peptide synthesis of a glucagon peptide using suitably protected amino acid derivatives or dipeptide derivatives, wherein said protected amino acid derivatives or dipeptide derivatives are activated by means of one or more coupling reagent mixtures comprising reagents selected for each step independently from the group consisting of:

(A) benzotriazolyl)tetramethyluronium tetrafluoroborate (TBTU) plus diisopropylethylamine (DIPEA);

(B) diisopropylcarbodiimide (DIC) plus cyano-hydroxy-imino-acetic acid ethyl ester (Oxyma);

(C) 3-(diethoxy-phosphoryloxy)-3H-benzo[d][1,2,3]tri-azin-4-one (DEPBT) plus DIPEA; and (D) DIC plus hydroxybenzotriazole (HOBt).

In one embodiment of the present invention, step a) comprises performing Fmoc-based solid phase peptide Synthesis of a glucagon peptide using suitably protected amino acid derivatives or dipeptide derivatives, wherein said protected amino acid derivatives or dipeptide derivatives are activated by means of one or more coupling reagent mixtures selected for each step independently from the group consisting of:

(A) benzotriazolyl)tetramethyluronium tetrafluoroborate (TBTU) plus diisopropylethylamine (DIPEA);

(B) diisopropylcarbodiimide (DIC) plus cyano-hydroxy-imino-acetic acid ethyl ester (Oxyma);

(C) 3-(diethoxy-phosphoryloxy)-3H-benzo[d][1,2,3]tri-azin-4-one (DEPBT) plus DIPEA; and (D) DIC plus hydroxybenzotriazole (HOBt).

The coupling of His derivatives is preferably carried out so as to avoid racemization. This side reaction can be reduced by three different approaches: 1) blocking of the N3 of the imidazole ring, 2) blocking of the N1 of the imidazole ring by electron withdrawing groups such as Boc or Tos, and 3) optimization of coupling conditions when using Fmoc-His(1-Trt)-OH. It is therefore recommended to use Fmoc-His(1-Trt)-OH, Boc-His(1-Trt)-OH, or Boc-His(1-Boc)-OH, most preferably Boc-His(1-Boc)-OH, in combination with either DIC/Oxyma or DEPBT/DIPEA to introduce an N-terminal His.

Therefore, in a preferred embodiment, the N-terminal histidine moiety is introduced into the glucagon peptide conjugated to the solid phase using an amino acid derivative selected from the group consisting of Boc-His(Boc)-OH, Boc-His(Trt)-OH, and Fmoc-His(Trt)-OH and a coupling reagent mixture comprising DEPBT plus DIPEA or DIC plus Oxyma.

It has surprisingly been found that the use of at least two Fmoc pseudoproline dipeptides advantageously suppresses peptide aggregation and hence the formation of by-products due to inefficient synthesis. Preferably, two pseudoproline dipeptides are introduced at two positions corresponding to or identical with two positions selected from the group consisting of ($Gly^4$-$Thr^5$ and $Phe^6$-$Thr^7$), ($Gly^4$-$Thr^5$ and $Thr^7$-$Ser^8$), ($Gly^4$-$Thr^5$ and $Tyr^{10}$-$Ser^{11}$), ($Gly^4$-$Thr^5$ and $Asp^{15}$-$Ser^{16}$), ($Phe^6$-$Thr^7$ and $Tyr^{10}$-$Ser^{11}$), ($Phe^6$-$Thr^7$ and $Asp^{15}$-$Ser^{16}$), ($Thr^7$-$Ser^8$ and $Tyr^{10}$-$Ser^{11}$), ($Thr^7$-$Ser^8$ and $Asp^{15}$-$Ser^{16}$), and ($Tyr^{10}$-$Ser^{11}$ and $Asp^{15}$-$Ser^{16}$) of the peptide of SEQ ID No: 1.

Therefore, in one aspect of the present invention, step a)—i.e. the step of providing a liquid composition C comprising a glucagon peptide and at least one unwanted component-comprises:

(a-i) providing a glucagon peptide conjugated to a solid phase, wherein at least the side chains of Glu, Asp, and Lys carry protecting groups and wherein the glucagon peptide conjugated to a solid phase comprises two pseudoproline dipeptides, preferably wherein the two pseudoproline dipeptides are introduced at positions corresponding to or identical with the positions selected from the group consisting of: $Gly^4$-$Thr^5$ and $Phe^6$-$Thr^7$, $Gly^4$-$Thr^5$ and $Thr^7$-$Ser^8$, $Gly^4$-$Thr^5$ and $Tyr^{10}$-$Ser^{11}$, $Gly^4$-$Thr^5$ and $Asp^{15}$-$Ser^{16}$, $Phe^6$-$Thr^7$ and $Tyr^{10}$-$Ser^{11}$, $Phe^6$-$Thr^7$ and $Asp^{15}$-$Ser^{16}$, $Thr^7$-$Ser^8$ and $Tyr^{10}$-$Ser^{11}$, $Thr^7$-$Ser^8$ and $Asp^{15}$-$Ser^{16}$, or $Tyr^{10}$-$Ser^{11}$ and $Asp^{15}$-$Ser^{16}$ of the peptide of SEQ ID No: 1; and (a-ii) cleaving the glucagon peptide from the solid phase and, preferably, removing the protection groups from the glucagon peptide.

As used in the context of the present invention, a pseudoproline dipeptide may be considered as a protection group. Preferably, such protection group is thus also removed in step (a-ii) of the method of the present invention.

The term "pseudoproline dipeptides" as used herein refers to temporary proline mimics, which can, e.g, be readily obtained from Ser and Thr containing dipeptides by oxazo-lidine formation and from Cys containing dipeptides by thiazolidine formation. The person skilled in the art is well-aware of such pseudoproline dipeptides. These dipeptides are one possible option to mitigate on-resin aggregation during SPPS. The 2,2-dimethyloxazolidines are smoothly cleaved by TFA and thus particularly suitable for Fmoc-SPPS. They are herein abbreviated as (Psi(Me,Me) pro).

In a particularly preferred embodiment, at least two pseudoproline dipeptide derivatives are used, which are selected from the group consisting of Fmoc-Gly-Thr(Psi (Me, Me)pro)-OH, Fmoc-Phe-Thr(Psi(Me, Me)pro)-OH, Fmoc-Thr(tBu)-Ser(Psi(Me, Me)pro)-OH, Fmoc-Tyr(tBu)-Ser(Psi(Me,Me)pro)-OH, and Fmoc-Asp(OtBu)-Ser(Psi (Me,Me)pro)-OH. Thus, step a) of the method disclosed herein may comprise performing Fmoc SPPS The term "positions corresponding to two positions selected from the group consisting of ($Gly^4$-$Thr^5$ and $Phe^6$-$Thr^7$), [ . . . ], and ($Tyr^{10}$-$Ser^{11}$ and $Asp^{15}$-$Ser^{16}$) of the peptide of SEQ ID No: 1" as used herein refers to two positions within the primary sequence of a glucagon peptide, which positions are considered homologous to the two selected positions of the peptide of SEQ ID NO: 1, based on a sequence alignment of said glucagon peptide with the peptide of SEQ ID NO: 1. Typically, the positions, which are displayed on top of each other in such an alignment are considered to be homologous, i.e. to correspond to each other. Typical sequence alignment tools such as BLAST or ClustalW are well known to the person skilled in the art.

Thus, the introduction of a pseudoproline moiety results in the provision of a solid-phase conjugated glucagon peptide, which is characterized by a reduced percentage of related impurities. In one aspect, the present application therefore provides a solid phase conjugated glucagon peptide, which comprises at least two pseudoproline dipeptides and wherein the side chain of the N-terminal His moiety is protected by a Boc- or Trt protecting group, in particular by a 1-Boc or 1-Trt protecting group. In another aspect, the present application therefore provides a solid phase conjugated glucagon peptide, which comprises at least two pseudoproline dipeptides and an N-terminal Boc-His(Boc) moiety. In another aspect, the present application therefore provides a solid phase conjugated glucagon peptide, which comprises at least two pseudoproline dipeptides and an N-terminal Boc-His(1-Trt) moiety. In a preferred embodiment, said solid phase conjugated glucagon peptide is further characterized by low contents of $Glu^{24}$-glucagon, des-$Ser^2$-glucagon and des-$Thr^5$-glucagon. In another preferred embodiment, said solid-phase conjugated glucagon peptide is characterized by a relative content of below 0.70% of des-$Ser^2$-glucagon, or of below 0.50% des-$Thr^5$-glucagon, or of below 0.70% $Glu^{24}$-glucagon.

In another preferred embodiment, said solid-phase conjugated glucagon peptide is characterized by a relative content of below 0.70% of des-$Ser^2$-glucagon, and of below 0.50% des-$Thr^5$-glucagon, and of below 0.70% $Glu^{24}$-glucagon. In another preferred embodiment, the said solid-phase conjugated glucagon peptide is characterized by a relative content of below 2.0% for any single deletion variant, which differs from the glucagon peptide of interest by a single amino acid. In another preferred embodiment, the said solid-phase conjugated glucagon peptide is characterized by a relative content of below 2.0% for each of des-His$^1$-glucagon, des-Ser$^2$-glucagon, des-Gln$^3$-glucagon, des-Gly$^4$-glucagon, des-Thr$^5$-glucagon, des-Phe$^6$-glucagon, des-Thr$^7$-glucagon, des-Ser$^8$-glucagon, des-Asp$^9$-glucagon, des-Tyr$^{10}$-glucagon, des-Ser$^{11}$-glucagon, des-Lys$^{12}$-glucagon, des-Tyr$^{13}$-glucagon, des-Leu$^{14}$-glucagon, des-Asp$^{15}$-glucagon, des-Ser$^{16}$-glucagon, des-Arg$^{17}$-glucagon, des-Arg$^{18}$-glucagon, des-Ala$^{19}$-glucagon, and des-Gln$^{20}$-glucagon. In another preferred embodiment, the said solid-phase conjugated glucagon peptide is characterized by a relative content of below 1.0% for each of des-His$^1$-glucagon, des-Ser$^2$-glucagon, des-Gln$^3$-glucagon, des-Gly$^4$-glucagon, des-Thr$^5$-glucagon, des-Phe$^6$-glucagon, des-Thr$^7$-glucagon, des-Ser$^8$-glucagon, des-Asp$^9$-glucagon, des-Tyr$^{10}$-glucagon, des-Ser$^{11}$-glucagon, des-Lys$^{12}$-glucagon, des-Tyr$^{13}$-glucagon, des-Leu$^{14}$-glucagon, des-Asp$^{15}$-glucagon, des-Ser$^{16}$-glucagon, des-Arg$^{17}$-glucagon, des-Arg$^{18}$-glucagon, des-Ala$^{19}$-glucagon, and des-Gln$^{20}$-glucagon. In another preferred embodiment, the said solid-phase conjugated glucagon peptide is characterized by a relative content of below 1.0% for at least 2 of des-His$^1$-glucagon, des-Ser$^2$-glucagon, des-Gln$^3$-glucagon, des-Gly$^4$-glucagon, des-Thr$^5$-glucagon, des-Phe$^6$-glucagon, des-Thr$^7$-glucagon, des-Ser$^8$-glucagon, des-Asp$^9$-glucagon, des-Tyr$^{10}$-glucagon, des-Ser$^{11}$-glucagon, des-Lys$^{12}$-glucagon, des-Tyr$^{13}$-glucagon, des-Leu$^{14}$-glucagon, des-Asp$^{15}$-glucagon, des-Ser$^{16}$-glucagon, des-Arg$^{17}$-glucagon, des-Arg$^{18}$-glucagon, des-Ala$^{19}$-glucagon, and des-Gln$^{20}$-glucagon.

In another preferred embodiment, the said solid-phase conjugated glucagon peptide is characterized by a relative content of below 2.0% for at least 4 of des-His$^1$-glucagon, des-Ser$^2$-glucagon, des-Gln$^3$-glucagon, des-Gly$^4$-glucagon, des-Thr$^5$-glucagon, des-Phe$^6$-glucagon, des-Thr$^7$-glucagon, des-Ser$^8$-glucagon, des-Asp$^9$-glucagon, des-Tyr$^{10}$-glucagon, des-Ser$^{11}$-glucagon, des-Lys$^{12}$-glucagon, des-Tyr$^{13}$-glucagon, des-Leu$^{14}$-glucagon, des-Asp$^{15}$-glucagon, des-Ser$^{16}$-glucagon, des-Arg$^{17}$-glucagon, des-Arg$^{18}$-glucagon, des-Ala$^{19}$-glucagon, and des-Gln$^{20}$-glucagon. The relative content of said impurities in the solid-phase conjugated glucagon is preferably determined by measuring the relative peak area (peak area of the impurity divided by total peak area of all peaks observed) in analytical UHPLC of the corresponding crude peptide.

When performing SPPS, capping may be performed to block unreacted amines from peptide bond formation in the following steps of synthesis, i.e., to avoid the formation of deletion variants of the sequence to be synthesized. This may be achieved by a short treatment of the peptide resin with a large excess of a highly reactive unhindered acid derivative, e.g. acetic anhydride or benzoyl chloride, and a base, e.g. pyridine, collidine, or DIPEA, optionally in the presence of an additive such as OxymaPure® or HOBt. Inter alia, the following capping compositions may be used: 1-15 eq. N-acetylimidazole in DCM; acetic anhydride/pyridine (1:1) in 2.5 to 25 volumes of DMF [i.e. (1:1:5) v/v/v to (1:1:50) v/v/v]; acetic anhydride/DIPEA (1:1) in 1 to 10 volumes of DMF [i.e. (1:1:2) v/v/v to (1:1:20) v/v/v]; 1-15 eq acetic anhydride and trietylamine in DCM; 1-5 eq N-(2-chlorobenzyloxycarbonyl)-succinimide and DIPEA in NMP/DCM (1:1); and 1-15 eq (Boc)$_2$O with 1-10 eq DIPEA in NMP. Capping will typically yield a truncated sequence, which generally differs considerably from the final peptide and can be readily separated. Preferably, systematic double coupling is followed by capping. At the end of the capping step, the reagents are typically filtered off and the resin is carefully washed, e.g. with DMF and optionally IPA, before proceeding to the next deprotection step.

Optionally, the progress of the SPPS reaction may be monitored using in process controls to ensure efficient Fmoc removal, coupling, and/or capping steps. Fmoc determination on one hand and determination of free amines on the other hand may result in complementary information. Taken together, these methods may enable efficient monitoring of each step of the SPPS process. Some of the common monitoring methods usable in the context of the present invention are exemplified below.

Optionally, the amount of Fmoc cleaved from the resin-bound peptide may easily be quantified, e.g., by spectrometric determination or by applying HPLC analysis.

The Fmoc cleavage reagent drained from the resin may be collected and the Fmoc concentration therein determined, e.g. by measuring the absorbance at 301 nm. Based on the amount of Fmoc cleaved off, the resin load, i.e. the original amount of Fmoc peptide on the resin, may be calculated. Further, to assess the completeness of Fmoc removal, a small sample of presumably Fmoc-deprotected resin may be subjected to an additional harsh Fmoc cleavage protocol in order to determine the amount of residual Fmoc removed by this treatment. In the alternative, a small scale test cleavage of the peptide from a resin sample may be carried out in order to assess the completeness of Fmoc removal. The resulting peptides may be analyzed by analytical RP-HPLC using a standard gradient, where Fmoc protected and free peptide sequences are usually well separated. Additionally or alternatively, the peptide sample may be analyzed by mass spectrometry, e.g. by LC-MS or MALDI-MS. Thin layer chromatography likewise may enable the detection of minute amounts of Fmoc peptides.

The amount of free amines on the resin may be assessed by various assays, including the colorimetric Kaiser (i.e. Ninhydrin), TNBS, Chloranil, and Bromophenol Blue tests. This is well-known to a person skilled in the art.

When the synthesis of the glucagon peptide by SPPS is completed, it is still conjugated to the resin. Thus, it is solid phase bound and at least partly side-chain protected. To obtain the glucagon peptide, it needs to be cleaved off the resin. Therefore, one aspect of the present invention is to provide a method for the production of a glucagon peptide, comprising cleaving the above-described solid phase conjugated glucagon peptide from the solid phase and, preferably, removing the protection groups from the glucagon peptide. This is represented, e.g., by step (ii) or step (a-ii) of cleavage of the glucagon peptide from the solid phase.

Most preferably, during this step, also most or all of the side chain protecting groups are concomitantly cleaved off the glucagon peptide, i.e., the peptide is deprotected.

Therefore, preferably, deprotection and cleavage from the resin, e.g. in step (a-ii), are carried out concomitantly by incubation with a cleavage composition comprising TFA and one or more scavengers.

In the context of the present application, the term "scavengers" is used to refer to compounds which are added to the reaction mixture in order to suppress side reactions during cleavage of a peptide from the resin after SPPS and/or during removal of protecting groups. Typical scavengers used in a cleavage composition are "thiol scavengers" (e.g. EDT, DTE, DTT, and beta-mercaptoethanol) and "silane scavengers" (e.g. TES and TIPS). Further commonly used scavengers comprise ethyl methyl sulfide, thioanisole, anisole, m- or p-cresol, 2-Me-indole, Ac-Trp-OMe, or trypt-amine. The person skilled in the art is well aware of a large variety of scavengers usable.

For cleaving the peptide off the resin and, preferably, removing the protection groups from the glucagon peptide, any composition suitable for this purpose may be used. Preferably, cleavage and deprotection is conducted by means of a composition comprising more than 50% (v/v) TFA, more preferably more than 75% (v/v) TFA, in particu-lar at least 80% (v/v) or even at least 90% (v/v) TFA. The composition may also comprise one or more scavengers. The composition may also comprise water. Preferably, the composition comprises TFA, water and one or more scav-engers. Particularly advantageous scavengers are thiol scav-engers such as EDT and/or silane scavengers such as, e.g., TIPS. The cleavage composition may comprise at least 80% TFA, preferably at least 90% TFA, and EDT. The cleavage composition may comprise at least 80% TFA, preferably at least 90% TFA, water, and EDT. The cleavage composition may comprise at least 80% TFA, preferably at least 90% TFA, water, and TIPS. The cleavage composition may comprise at least 80% TFA, preferably at least 90% TFA, water, TIPS and EDT. Exemplary, compositions for use in the context of the present invention may be selected from the group consisting of TFA/water/TIPS (90:5:5) v/v/v, TFA/water/TIPS (95:2:3) v/v/v, TFA/water/phenol (90:5:5) v/v/v, TFA/m-cresole (95:5) v/v, TFA/m-cresole (92:8) v/v, TFA/water/EDT (90:5:5) v/v/v, TFA/TIPS/DTE/water (88/2/5/5) v/v/w/w; TFA/water/DTE (90/4/6) v/v/w; TFA/water/EDT/TIPS (90:5:2.5:2.5) v/v/v/V, TFA/water/EDT/TIPS (90:4:3:3) v/v/v/V, TFA/water/EDT (92:4:4) v/v/V, TFA/water/EDT (85:5:10) v/v/v, TFA/thioanisole/anisole/EDT (90:5:3:2) v/v/v/v, and TFA/thioanisole/water/phenol/EDT (82.5:5:5:5:2.5) v/v/v/v/V.

The person skilled in the art will routinely optimize the compositions for use in the context of the present invention depending on the amino acid composition of the glucagon peptide in question and will envisage the optional use of one or more scavengers such as, inter alia, DTE, EDT, TES, TIPS, 2-mercaptoethanol, dimethyl sulfide, ethyl methyl sulfide, m- or p-cresol, 2-Me-indole, Ac-Trp-OMe, Phenol, or tryptamine.

The step of cleaving the glucagon peptide off the resin and, preferably, removing the protection groups from the glucagon peptide, e.g. step (a-ii), may be carried out at any conditions suitable for this purpose. Cleavage is preferably carried out (preferably under inert gas) by incubating the washed resin with the cleavage composition for about 1 to 4 h and/or at a temperature of 0 to 32° C. Exemplarily, cleavage may be carried out (preferably under inert gas) by incubating the washed resin with the cleavage composition for up to 1, up to 1.5, up to 2, up to 2.5, up to 3, up to 3.5 or up to 4 h or longer than 4 h at a temperature of about 0 to 4° C., 4 to 10° C., 10-15° C., 15 to 25° C., or 25 to 35° C. Exemplarily, cleavage may be carried out (preferably under inert gas) by incubating the washed resin with the cleavage composition for up to 1, up to 1.5, up to 2, up to 2.5, up to 3, up to 3.5 or up to 4 h or longer than 4 h at a temperature of about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32° C.

It may be recommendable to add one or more agents selected from the group consisting of iodide salts (e.g. ammonium iodide), dimethyl sulfide, 1,4-dithiothreitol (DTT), trimethylsilylbromide, and ascorbic acid to the sus-pension comprising the resin. This may be done, e.g., at the onset of the incubation of peptide resin and cleavage composition, or after incubating the peptide resin with the cleavage composition for a certain time. Without wishing to be bound by any theory, it is believed that this avoids and/or reverts oxidation of the S-methyl thioether group of the methionine side chain.

The resin is then separated, usually by filtration, from the solution S obtained by cleaving the peptide off the resin and, preferably, removing the protection groups from the gluca-gon peptide, e.g. in step (a-ii). Said solution S comprises the glucagon peptide and the reagents used for cleavage (e.g., TFA, water, scavengers, reducing agents, and residuals of the protecting groups cleaved off the peptide).

Optionally, the resin is rinsed after filtration, e.g. with concentrated TFA or with concentrated TFA plus scaven-gers. Optionally, the additional rinsing solutions may also form part of the solution S, i.e., they may be pooled with the solution obtained directly after cleavage of the peptide from the resin.

The person skilled in the art will note that it is desirable to isolate the glucagon peptide from the solution S, thereby obtaining a crude peptide (typically present as the TFA salt). This is preferably performed by precipitation of the gluca-gon peptide by means of an anti-solvent. Preferred anti-solvents comprise diethyl ether, isopropyl ether (IPE), methyl tert. butyl ether (MTBE), and mixtures of IPE with acetonitrile. In a preferred embodiment, IPE is used. Pref-erably, the volume ratio of solution S to antisolvent is in the range of 1:5 to 1:15, e.g. 1:5, 1:8, 1:10, 1:12, or 1:15. In other words: one volume of solution S may be mixed with an amount of antisolvent corresponding to, e.g., 5, 6, 7, 8, 9, 10, 11, 12, 13, 14, or 15 volumes.

The step of precipitation of the glucagon peptide out of the solution S (step (a-iii)) may be conducted at any tem-perature and any time interval suitable for this purpose. Exemplarily, precipitation of the glucagon peptide (step (a-iii)) is carried out at a temperature in the range of about -5° C. to 10° C., preferably about 0° C. to 10° C. Suitable temperature ranges may be about -5-0° C., -2.5-2.5° C., 0-5° C., 2.5-7.5° C., or 5-10° C. Exemplarily, the precipi-tation is carried out for a time interval of about 30 to 360 min, e.g. about 30, 60, 90, 120, 150, 180, 210, 240, 270, 300, 330, or 360 min. The solution S obtained by cleaving the peptide off the resin and, preferably, removing the protection groups from the glucagon peptide (e.g. in step (a-ii)) and the anti-solvent may be mixed by any means known in the art and in any order. For example, the anti-solvent may be added to the solution S. This may be achieved by adding it at once or by adding it dropwise and/or by means of a slow flow. Alternatively, the solution S may be added to the anti-solvent. This may be achieved by adding it at once or by adding it dropwise and/or by means of a slow flow. The person skilled in the art is well aware of how to conduct such precipitation steps.

The precipitate comprising the glucagon peptide is then formed as a suspension in the anti-solvent, wherein said suspension further comprises the reagents of the cleavage composition (e.g., TFA, water, and scavengers) as well as the residuals of the protecting groups cleaved off the peptide.

The precipitate comprising (or essentially consisting of) the glucagon peptide may then be isolated from the crude suspension by any means known for such purpose in the art.

Filtration may be any filtration method known in the art, such as, e.g., dead-end filtration or cross-flow filtration. As used herein, the terms "cross-flow filtration", "crossflow filtration", "tangential flow filtration" or "tangential filtra-tion" may be understood interchangeably. The filter may be of any material known in the context of filtration in the art, such as, e.g., plastic (e.g., nylon, polystyrene), metal, alloy, glass, ceramics, cellophane, cellulose, or composite material. The filter may be hydrophobic or hydrophilic. The surface of the filter may be neutral or positively charged or negatively charged.

Centrifugation may be understood in the broadest sense as any means wherein the sedimentation of the suspended precipitate is accelerated. Exemplarily, a centrifugal force of up to 100×g, at least 100×g, at least 1,000×g, at least 2,500×g, at least 5,000×g, at least 7,500×g, at least 10,000×g, at least 15,000×g, at least 25,000×g, or at least at least 50,000×g may be used. By means of centrifugation, a cake comprising (or (essentially) consisting of) the crude glucagon peptide is formed. Optionally, the cake may be resuspended in an anti-solvent which may be identical or different to the above-referenced anti-solvents. Optionally, centrifugation and resuspending the pellet in an anti-solvent may be reiterated several times which may increase the purity of the crude glucagon peptide further.

A crude peptide precipitate may comprise at least 30% (w/w), preferably at least 40% (w/w), more preferably at least 50% (w/w), more preferably at least 60% (w/w), more preferably at least 70% (w/w), even more preferably at least 80% (w/w), even more preferably at least 90% (w/w), in particular at least 95% (w/w) or even 100% (w/w) of the glucagon peptide in the dry state. Typically, a crude peptide precipitate comprises 40-70% (w/w) of the glucagon peptide in the dry state.

Preferably, the crude peptide obtained by the method of the present invention can be subjected to further purification by one or more preparative process steps in order to obtain the composition C.

Generally speaking, TFA cleavage of any peptide from the resin may result in formation of side products such as carbamates and TFA esters. It can therefore be advantageous to subject a crude peptide to a decarboxylation reaction and/or to ester hydrolysis. This may, exemplarily, be achieved by subjecting the crude peptide to a high pH treatment such as, e.g., a pH of at least 7.2, at least 8.0, at least 8.5, at least 9, at least 9.5, at least 10, at least 10.5, at least 11, or at least 11.5. Alternatively or additionally, decarboxylation reactions may be performed in mildly acid conditions such as, e.g. a pH of 6.0 to 7.0, pH of 5.5. to 6.5, a pH of 5.0 to 6.0, a pH of 4.0 to 5.0, a pH of 3.0 to 4.0, or a pH or 2.0 to 3.0. Optionally, said treatments may be accompanied by a heat treatment, e.g., at a temperature of 25-70° C., for example at 25, 30° C., 35° C., 40° C., 45° C., 50° C., 55° C., 60° C., 65° C., or 70° C. Treatment times may vary between 2 and 120 min, e.g. 2, 5, 10, 20, 30, 40, 50, 60, 70, 80, 90, 100, 110, or 120 min.

Depending on the specific case, it may be advantageous to subject the product of TFA cleavage to a protocol involving one or more of the following steps: ca. 30 min incubation at pH 2.0-3.0, 55° C.; ca. 40 min incubation at pH 7-7.5, 40° C.; ca. 60 min incubation at 45° C., pH of 2.0-4.0; ca. 90 min incubation at 50° C., pH of 2.0-4.0; ca. 70 min incubation at 30° C. at a pH of 5.4-6.6; ca. 90 min incubation at 45° C., pH of 6.6-7.4; 10 min incubation at alkaline pH (e.g. a pH of at least 10.2), 45-25° C.; 10 min incubation at pH 10.4, 35° C.; 2 min incubation at 30-40° C., pH. 11.0. 5 min incubation at 25° C., pH 11.8. It may be advantageous to dissolve the crude peptide precipitate in diluted acids, e.g. hydrochloric acid, acetic acid, trifluoro acetic acid, or diluted bases, e.g. aqueous NaOH, ammonia, phosphate, TEAP for decarboxylation and/or TFA ester cleavage. The skilled person will routinely chose suitable conditions. It should be noted that the teachings of this paragraph are likewise applicable to the preparation of glucagon-like peptides and their analogs and derivatives, e.g. to the preparation of GLP-1 analogs and GLP-2 analogs.

Therefore, in an embodiment of the invention, the step a), i.e. the step of providing a liquid composition C comprising a glucagon peptide and at least one unwanted component, comprises subjecting a glucagon peptide to decarboxylation and/or ester hydrolysis reactions.

In another embodiment of the invention, the step a) comprises subjecting a sample comprising a glucagon peptide to a reversed phase high performance liquid chromatography (RP-HPLC) purification, wherein a hydrocarbon bonded silica is used as a stationary phase, an aqueous mobile phase comprising trifluoroacetic acid and acetonitrile is used, and elution is effected by gradually increasing the acetonitrile concentration within the mobile phase while collecting fractions containing the glucagon peptide.

Such a pre-purification step may preferably involve a RP-HPLC purification using a Buffer A comprising 0.1% (v/v) aqueous TFA and a Buffer B comprising 60% (v/V) acetonitrile in 0.1% aqueous TFA. In one embodiment, elution is effected by a gradient in acetonitrile concentration from 12% (v/v) to 60% (v/v). In one embodiment, a C18 stationary phase is used. In one embodiment, the mobile phase comprises 0.5 to 0.2% TFA and elution is effected by a linear gradient from 12% (v/v) acetonitrile to 60% (v/v) acetonitrile.

Further means for purification and separation, which may optionally be used in the step a) comprise, e.g., one or more electrophoretic methods (e.g., gel electrophoresis or capillary (CE) electrophoresis), one or more additional precipitation-based methods (e.g., salting in or salting out), one or more dialytical methods (dialysis), and/or one or more chromatographic methods (e.g., gel permeation chromatography (GPC), size exclusion chromatography, Ion exchange chromatography (IEC), high performance liquid chromatography (HPLC), reversed phase HPLC (RP-HPLC), fast protein liquid chromatography (FPLC), Flash Chromatography (flash), Rapid Refluid Liquid Chromatography (RRLC), Rapid Separation Liquid Chromatography (RSLC), Ultra Fast Liquid Chromatography (UFLC), reversed phase UFLC (RP-UFLC), Ultra Performance Liquid Chromatography (UPLC) or reversed phase UPLC (RP-UPLC), counter current chromatography, continuous chromatography).

In one embodiment of the invention, the step a) comprises the steps of:

a-i) providing a glucagon peptide conjugated to a solid phase, wherein at least the side chains of Glu, Asp, and Lys carry protecting groups, by performing Fmoc-based Solid Phase Peptide Synthesis of a glucagon peptide using suitably protected amino acid derivatives or dipeptide derivatives, wherein said protected amino acid derivatives or dipeptide derivatives are activated by means of one or more coupling reagent mixtures comprising reagents selected for each step independently from the group consisting of:

(A) (benzotriazolyl)tetramethyluronium tetrafluoroborate (TBTU) plus diisopropylethylamine (DIPEA);

(B) diisopropylcarbodiimide (DIC) plus cyano-hydroxyimino-acetic acid ethyl ester (Oxyma);

(C) 3-(diethoxy-phosphoryloxy)-3H-benzo[d][1,2,3]triazin-4-one (DEPBT) plus DIPEA; and (D) DIC plus hydroxybenzotriazole (HOBt), further wherein an N-terminal histidine moiety is introduced into the glucagon peptide conjugated to the solid phase using an amino acid derivative selected from the group consisting of Boc-His(Boc)-OH, Boc-His(Trt)-OH, and Fmoc-His(Trt)-OH, optionally further wherein at least two pseudoproline dipeptides are used;

a-ii) cleaving the glucagon peptide from the solid phase (and, preferably, removing the protection groups from the glucagon peptide) by incubation with a cleavage composition comprising at least 50% TFA and one or more scavenger(s), and/or wherein one or more agents selected from the group consisting of iodide salts, dimethyl sulfide, 1,4-dithiothreitol (DTT), trimethylsi-lylbromide, and ascorbic acid is or are added to the peptide solution after cleavage; and a-iii) isolating the peptide from the resulting solution by precipitation.

In another embodiment of the invention, the step a) comprises said steps a-i) through a-iii) and additionally the step a-iv) of subjecting the peptide precipitate obtained in step a-iii) to a reversed phase high performance liquid chromatography (RP-HPLC) purification, wherein a hydrocarbon bonded silica is used as a stationary phase, an aqueous mobile phase comprising trifluoroacetic acid and acetonitrile is used, and elution is effected by gradually increasing the acetonitrile concentration within the mobile phase while collecting fractions containing the glucagon peptide. In one embodiment, step a-iv) involves a RP-HPLC purification using a Buffer A comprising 0.1% (v/v) aqueous TFA and a Buffer B comprising 60% acetonitrile in 0.1% (v/v) aqueous TFA.

In one embodiment, elution is effected by a gradient in acetonitrile concentration from 12% (v/v) to 60% (v/v). In one embodiment, a C18 stationary phase is used in step a-iv). In some embodiments, the above mobile phases are used with a C8 stationary phase, e.g. with 120 Å pore size and 15-30 micrometer particle size. In some alternative embodiments, the above mobile phases are used with a C18 stationary phase, e.g. with 120 Å pore size and 15-30 micrometer particle size.

More preferably, the whole amount of glucagon contained in the composition C is obtained by the above methods.

In a preferred embodiment of the invention, step a) of the purification method involves obtaining a dried crude glucagon peptide precipitate and dissolving said dried precipitate, in order to obtain a liquid composition C comprising glucagon and at least one unwanted component. For example the liquid composition C may comprise a crude glucagon peptide in diluted acetic acid at a pH between about 2 and about 4.

In the context of the present invention, the term "purified" is used to designate peptide compositions which have been subjected to specific purification steps, e.g. to preparative chromatography. Such compositions may be highly or partially purified.

Unless noted otherwise, peptide purity is indicated herein as "HPLC purity", i.e. as relative peak area observed in analytical reversed phase high performance liquid chromatography (RP-HPLC) with UV detection at a wavelength between 205 and 230 nm, i.e. at the absorption maximum of the peptide bond. In other words, the value is determined as % area of a given peak area divided by the sum of the areas of all observed peaks in a chromatogram obtained by analytical RP-HPLC with UV detection at a wavelength between 205 and 230 nm. This measure is common practice in the field, and the skilled person will routinely devise a product specific RP-HPLC protocol and perform the quantification according to the established guidelines set out in the United States Pharmacopeia. The suitability of the RP-HPLC protocol for the detection of peptidic contaminations is routinely assessed by determining the peak purity by LC-MS.

Under the assumption that, due to their similar structure, all peptidic components have the same absorption, the RP-HPLC purity can be used as a proxy for a purity expressed as mass percentage [% (w/w)].

Likewise, the relative content of a peptide (be it a wanted or unwanted component) may be determined relative peak area observed in analytical reversed phase high performance liquid chromatography (RP-HPLC) with UV detection at a wavelength between 205 and 230 nm, i.e. at the absorption maximum of the peptide bond. In other words, the value is determined as % area of a given peak area divided by the sum of the areas of all observed peaks in a chromatogram obtained by analytical RP-HPLC with UV detection at a wavelength between 205 and 230 nm, using a suitable protocol as set out above.

The skilled person is well aware of how to prepare samples for chromatographic purification. For example, a dried crude glucagon preparation may be dissolved by gentle stirring in an aqueous phase while adjusting temperature and pH as appropriate. As further examples, the sample may be kept under inert gas or subjected to ultrasound treatment, may be subjected to decarboxylation reactions, may be subjected to TFA ester hydrolysis, and/or may be separated from non-liquid components by filtration or centrifugation. The sample concentration may be adjusted, inter alia, by drying, freeze-drying, partial evaporation of solvent, or ultrafiltration, and/or by dissolving or diluting the peptide preparation in a sample loading buffer, as the case may be.

Reversed phase high performance liquid chromatography (RP-HPLC) is well-known and widely used for peptide purification and analysis of peptide samples, i.e. for preparative as well as analytical purposes. The technique is based on hydrophobic association between the various components of a sample and a hydrophobic stationary phase, which association is disrupted by an agent, e.g. a solvent, comprised in the mobile phase. Differential elution of the sample's components is usually achieved by gradually increasing the concentration of the agent, e.g. a solvent, within the mobile phase.

From a practical perspective, this gradient is usually obtained by varying the proportions of a first and second elution buffer making up the mobile phase:

The first buffer, dubbed Buffer A by convention, comprises low amounts of the solvent in a suitable aqueous buffer, while the second buffer, dubbed Buffer B by convention, comprises high amounts of the solvent in said aqueous buffer. Hence, by increasing the proportion of Buffer B in the mobile phase, more hydrophobic components can be eluted from the stationary phase.

As used herein, the term HPLC also includes ultra high performance liquid chromatography (UHPLC, also designated as UPLC). In one preferred embodiment, HPLC is UHPLC. More preferably, UHPLC is reversed phase UHPLC and may thus also be designated as RP-UHPLC. Therefore, in a particularly preferred embodiment, HPLC is RP-UHPLC.

In the context of the present application, the expression "hydrocarbon bonded silica" refers to stationary chromatographic phases made from porous silica particles or silica gels having chemically bonded hydrocarbon moieties at their surface. It is understood that the type of chemical bond as well as the chemical nature of the bonded hydrocarbon moieties may vary. For example, a stationary phase for use with the present application may be made from porous silica particles having chemically bonded hydrocarbon moieties of 4 to 18, preferably 8 to 18, carbon atoms. Such hydrocarbon moieties are preferably linear alkyl chains. Preferred types of hydrocarbon bonded silica have hydrocarbon moieties with four (C4), six (C6), eight (C8), ten (C10), twelve (C12), fourteen (C14), sixteen (C16), or eighteen (C18) carbon atoms. Particularly preferred types of hydrocarbon bonded silica have unbranched alkyl chains of four (C4), eight (C8), twelve (C12) or eighteen (C18) carbon atoms, i.e. butyl, octyl, dodecyl, or octadecyl moieties. C8 bonded silica, in particular n-octyl bonded silica, and/or C18 bonded silica, in particular n-octadecyl bonded silica, are even more preferred stationary phases for use in steps b), c), and optionally d) of a method according to the present invention. The stationary phase used in steps b) and c) may be the same or different in each of the steps. Preferably the stationary phase is the same. Particularly preferably, C18 bonded silica is used as a stationary phase in step b) and/or step c), and/or wherein the same stationary phase is used in steps b) and c), preferably wherein the identical column is used for steps b) and c). This option of using a single stationary phase (i.e., a single column) in steps b) and c) enables a particularly cost-efficient procedure.

In the context of the present application, the expression "C8 bonded silica" is used to designate stationary chromatographic phases made from porous silica particles or silica gels having at their surface chemically bonded C8 hydrocarbon moieties, preferably linear octyl, i.e. n-octyl, moieties. Further, the expression "C12 bonded silica" is used to designate stationary chromatographic phases made from porous silica particles or silica gels having at their surface chemically bonded C12 hydrocarbon moieties, preferably linear dodecyl, i.e. n-dodecyl, moieties. Likewise, the terms "C18 bonded silica" or "ODS" are used herein interchangeably to refer to stationary chromatographic phases made from porous silica particles or silica gels having at their surface chemically bonded C18 hydrocarbon moieties, preferably linear octadecyl, i.e. n-octadecyl, moieties.

A wide range of hydrocarbon bonded silica materials is commercially available. Examples of stationary phases which can be used in present invention are Daisogel™ C18 ODS, Daiso ODS-Bio, Daiso-ODS-A-HG C18, Daisogel™ C8-Bio, YMC ODS-A, YMC Triart C8-L, Luna C8, Luna C18, Kromasil™ C18, and Kromasil™ C8 produced by Daiso, YMC, Phenomenex, and AkzoNobel, respectively.

The silica particles may be of 2 to 200 micrometer, preferably 2.5 to 20 micrometer, preferably 5-15 micrometer, and most preferably 10 micrometer, in diameter and may have a pore size of 50 to 1000 Å, preferably of 80 to 400 Å, preferably of 100 to 300 Å, most preferably of (about) 100 Å.

It is good practice to flush the stationary phase between runs with a suitable solution so as to remove any impurities, which are still bound to the column and may compromise the quality of subsequent peptide batches. Various such cleaning protocols have been described for this purpose, including flushing with aqueous solutions of NaOH or formic acid (cf., e.g., WO 2004/089504). The present inventors found rinsing the stationary phase with aqueous solutions of TFA comprising acetonitrile before column loading is beneficial for the quality of the purified glucagon peptide in that it reduces aggregation. Particularly suitable are mixtures comprising TFA, and more than 20%, e.g. 30, 40, 50, 60, 70, 80, or 90% (v/v) of acetonitrile in aqueous solution. The concentration of TFA is preferably chosen form the range of 0.05% (v/v) to 1.0% (v/v). For example, the mixture may comprise more than 50% ACN and 0.05-1.0% TFA.

Example mixtures include, but are not limited to the following: 1% (v/v) TFA and 25% ACN in water; 1% (v/v) TFA and 30% ACN in water; 1% (v/v) TFA and 50% ACN in water; 1% (v/v) TFA and 70% ACN in water; 1% (v/v) TFA and 90% ACN in water; 0.5% (v/v) TFA and 25% ACN in water; 0.5% (v/v) TFA and 40% ACN in water; 0.5% (v/v) TFA and 50% ACN in water; 0.5% (v/v) TFA and 60% ACN in water; 0.5% (v/v) TFA and 70% ACN in water; 0.5% (v/v) TFA and 80% ACN in water; 0.1% (v/v) TFA and 25% ACN in water; 0.1% (v/v) TFA and 40% ACN in water; 0.1% (v/v) TFA and 50% ACN in water; 0.1% (v/v) TFA and 60% ACN in water; 0.1% (v/v) TFA and 70% ACN in water; 0.1% (v/v) TFA and 80% ACN in water; 0.1% (v/v) TFA and 90% ACN in water; 0.05% (v/v) TFA and 40% ACN in water; 0.05% (v/v) TFA and 50% ACN in water; 0.05% (v/v) TFA and 60% ACN in water; 0.05% (v/v) TFA and 70% ACN in water; 0.05% (v/v) TFA and 80% ACN in water. A method according to the present invention may therefore comprise the step of rinsing the stationary phase with an aqueous solution comprising TFA and acetonitrile prior to loading with the liquid composition C and/or prior to loading with the pooled glucagon peptide containing fractions obtained in step b).

This aspect of the present invention is analogously applicable to the purification of other peptides, in particular to the purification of glucagon-like peptides, e.g. to analogs and derivatives of GLP-1 and GLP-2 such as exenatide, lixisenatide, liraglutide, semaglutide, teduglutide, etc.

Therefore, one aspect of the present invention relates to a process for regenerating a chromatographic stationary phase wherein said chromatographic stationary phase is contacted with a regeneration solution comprising trifluoroacetic acid, water, and acetonitrile subsequent to a chromatographic purification of a peptide-containing sample.

Another aspect of the present invention relates to a peptide purified using a chromatographic stationary phase, which was regenerated using the above process.

The mobile phases used in the RP-HPLC steps of the present invention generally comprise an aqueous component and acetonitrile as a solvent. Additional components such as organic modifiers may be present. Elution is usually effected by gradually increasing the concentration of the acetonitrile as a solvent.

Without wishing to be bound by any theory, it is believed that the solvent competes with the association of the components of composition C to the stationary phase. In order to maintain a linear velocity, the skilled practitioner will adjust the flow rate of the mobile phase depending on the column diameter and taking account of the specifications of the equipment and stationary phase employed.

Step b) of the method according to the present invention, i.e. the first dimension of the RP-HPLC purification scheme, is carried out at a pH value between 6.5 and 7.5, e.g. at a pH value of 6.5, 6.6, 6.7, 6.8, 6.9, 7.0, 7.1, 7.2, 7.3, 7.4, or 7.5, preferably at a pH value between 6.7 and 7.2. The pH value is adjusted at the temperature at which the step will be carried out by use of concentrated phosphoric acid and trimethylamine (TEA) in the aqueous component of the mobile phase. Preferably, the phosphate anion is present at a concentration of 5 to 50 mM, e.g. at about 10, 20, 30, 40, or 50 mM. It is understood that any type of acetonitrile gradient may be used for the elution of glucagon from the stationary phase and that the gradient profile impacts the purification achievable in this step.

In a preferred embodiment, the elution in step b) is effected by a gradient of increasing the acetonitrile content from 2 to 4% (v/v) acetonitrile to 30 to 50% (v/v) acetonitrile.

In another preferred embodiment, the elution in step c) is effected by a gradient of increasing the acetonitrile content from 2 to 4% (v/v) acetonitrile to 40 to 60% (v/v) acetonitrile.

In a more preferred embodiment, the elution in step b) is effected by a gradient of increasing the acetonitrile content from 2 to 4% (v/v) acetonitrile to 30 to 50% (v/v) acetonitrile, and the elution in step c) is effected by a gradient of increasing the acetonitrile content from 2 to 4% (v/v) acetonitrile to 40 to 60% (v/v) acetonitrile.

It will therefore be routinely adapted by the skilled person to the specific experimental setup. In a preferred embodiment, the glucagon peptide is eluted in step b) by a gradient from 3-20% acetonitrile to 40-50% (v/v) acetonitrile, e.g. a gradient from 3 to 40% (v/v) acetonitrile, or from 7 to 43% (v/v) acetonitrile. Particularly preferred is a linear gradient.

In a more preferred embodiment, the elution in step b) is effected by a gradient of 3 to 40% (v/v) acetonitrile, and/or wherein elution in step c) is effected by a gradient of 3 to 50% (v/v) acetonitrile.

Step c) of the method according to the present invention, i.e. the second dimension of the RP-HPLC purification scheme, is preferentially carried out at a pH value selected from the range of about 2 to 4, preferentially about 2 to 3, e.g. about 2.0, 2.1, 2.2, 2.3, 2.4, 2.5, 2.6, 2.7, 2.8, 2.9, or 3.0. The pH value may be determined by the presence of 0.5-5% (v/v) acetic acid in the aqueous component of the mobile phase. In a preferred embodiment, the acetic acid concentration within the mobile phase used in step c) is selected from the range of 0.5-5% (v/v), preferably 1-3% (v/v), e.g. 1, 2, or 3% (v/v). It is understood that any type of acetonitrile gradient may be used for the elution of glucagon from the stationary phase and that the gradient profile impacts the purification achievable in this step. In a preferred embodiment, the gradient in step c) is from 3 to 50% (v/v) acetonitrile. Particularly preferred is a linear gradient from 3 to 50% (v/v) acetonitrile. E.g, a linear gradient from 3 to 50% acetonitrile may be used.

In a preferred embodiment, the method further comprises step d) of performing an anion exchange, preferably wherein acetate is replaced by chloride and/or wherein the anion exchange is achieved by lyophilization, ultrafiltration, dialysis, solid phase extraction, reversed-phase chromatography or by ion exchange chromatography.

Step d) may be performed by any anion exchange method known in the art of peptide manufacture.

The skilled person will routinely combine the methods of the present invention with suitable read-out techniques. For example, chromatographic steps may be monitored by following the UV absorbance of the eluate at a wavelength of 205-230 nm or 280 nm, and/or by following the eluate's conductivity. Moreover, chromatography may be combined with online or offline analysis by mass spectrometry, size exclusion UHPLC, ion exchange UHLPC, and/or reversed phase UHPLC, enzyme-linked immunosorbent assays (ELISA), and/or cell-based functional assays.

In order to avoid deterioration of the peptide quality, the skilled person will carefully and routinely optimize the conditions of the purification steps including the sample storage. To this end, fractions may be, inter alia, pooled, precipitated, spray-died, freeze-dried, frozen, refrigerated, diluted, concentrated, and/or mixed with stabilizing buffers, bases, acids, or other substances. It is good practice to handle sensitive materials under stabilizing conditions. For example, it may be advantageous to work at reduced temperature, e.g. in the range of 4° C. to 15° C. in order to compensate for otherwise destabilizing conditions. As a further example, it may be advantageous to freeze-dry glucagon preparations, preferably at a pH selected from a range of 6.6-7.9, preferably 7.0 to 7.8, and most preferably 7.0 to 7.5. As another example, it may be advantageous to dilute fractions already during collection and/or to adjust the temperature and buffer conditions during elution. Glucagon is known to be more stable at reduced temperature, reduced concentration, and slightly acidic pH.

In a preferred embodiment of the invention, all or parts of the chromatographic purification steps b) and/or c) and/or step a-iv), if present, is/are carried out at a temperature selected from the range of 4-28° C., e.g. 15-28° C., 4-20° C., or 4-10° C. Likewise, all or parts of any optional further purification steps, e.g. the salt exchange step d), may be carried out at a temperature selected from the range of 4-28° C., preferably 4-20° C., and most preferably 4-10° C.

In a particularly preferred embodiment, the method of the present invention comprises:

a) Providing a liquid composition C comprising glucagon and at least one unwanted component, optionally dissolved in aqueous acetic acid of a pH selected from the range of 2.0 to 4.0;

b) Subjecting the composition C to a first reversed phase HPLC purification at a pH of about 7, wherein a hydrocarbon bonded silica is used as a stationary phase, a mixture comprising acetonitrile and an aqueous triethylammonium phosphate buffer at a concentration of 5 to 50 mM is used as a mobile phase, and elution is effected by gradually increasing the acetonitrile concentration within the mobile phase from 3 to 50% (v/v) acetonitrile while collecting glucagon peptide containing fractions; and c) Subjecting the pooled glucagon peptide containing fractions obtained in step b) to a second reversed phase HPLC purification, wherein a hydrocarbon bonded silica is used as a stationary phase, a mobile phase comprising acetic acid at a concentration of 0.005-0.05% (v/v) and acetonitrile is used, and elution is effected by gradually increasing the acetonitrile concentration within the mobile phase from 3 to 50%, while collecting fractions containing the purified glucagon peptide;

d) Optionally, subjecting the glucagon peptide obtained in step c) to an ion exchange step, wherein acetate is replaced by chloride wherein the steps b) and c) and, if present, step d) are carried out at a temperature selected from the range of 4-25° C.;

wherein preferably the stationary phase used in steps b) and c) is C8 bonded silica or C18 bonded silica.

As is shown in the examples below, the methods of the present invention enable the preparation of a very pure glucagon peptide, and purities above 99.0% can be routinely achieved. Nevertheless, traces of several deletion products could be detected.

These are in particular traces of peptides consisting of 26 to 28 continuous amino acids, which differ from the glucagon peptide's molecular structure in that they are lacking up to three amino acids out of the primary sequence of the glucagon peptide backbone (e.g. SEQ ID NO: 1), In other words, deletion variants of the glucagon peptide of SEQ ID NO: 1 may be defined as peptides of 26 to 28 amino acid moieties in length, which share at least 89% homology to SEQ ID NO: 1, calculated over the entire length of SEQ ID NO: 1.

The person skilled in the art will immediately understand that such glucagon deletion variants may optionally, but not necessarily, be truncated at the N- and/or C-terminal amino acid moieties. Additionally or alternatively, also non-terminal amino acid moieties may be missing. As mentioned above, sequence homology may be understood as sequence homology determined by BLAST (Basic Local Alignment Search Tool) of the National Center for Biotechnology Information (NCBI) in the version of the filing date of the present application. That means that each amino acid moiety is aligned to its counterpart in the sequence to be compared, sparing missing amino acid moieties in between and percentage homology is calculated over the entire length of SEQ ID NO: 1.

In the experiments conducted, no peptidic contaminant was detected in the final peptide product at a relative abundance above 0.5%, determined as relative peak area measured by RP-UHPLC at 220 nm (cf., exemplifying FIG. 3). This also reflects an aspect and preferred embodiments of the present invention. The relative peak area was determined as % area of a given peak area divided by the sum of the areas of all observed peaks in a chromatogram obtained by analytical RP-HPLC with UV detection at 220 nm. This can be done using any product-specific RP-HPLC protocol suitable for the detection of peptidic contaminants. The suitability of the analytical method is routinely assessed in terms of principal peak purity determined by LC-MS. In order to demonstrate the suitability of a given analytical protocol, spike experiments are routinely performed, where the contaminations to be detected are artificially added to a sample.

The person skilled in the art will immediately understand that, due to their similar structure, all peptidic components have the same or at least comparable response factors, such that the relative peak area measured by RP-HPLC at 220 nm correlates well to the relative abundance of a given peptide expressed in weight percent relative to the summed mass of all peptide components, indicated in % (w/w).

Therefore, a further aspect of the present invention relates to a composition GC comprising a glucagon peptide obtainable from a method according to any embodiment of the present invention, characterized in that said composition contains the glucagon peptide at a purity above 99.0%, determined as the relative peak area observed in analytical RP-HPLC with UV detection at 220 nm, and does not contain more than 0.5%, determined as the relative peak area observed in analytical RP-HPLC with UV detection at 220 nm, of any single glucagon derivative, glucagon truncation variant, derivative of a glucagon truncation variant, glucagon deletion variant, or derivative of a glucagon deletion variant.

Preferably, the composition GC contains glucagon at a purity above 99.1%, above 99.2%, above 99.3%, above 99.4%, above 99.5%, above 99.6%, above 99.7%, above 99.8% or above 99.9%, determined as the relative peak area observed in analytical RP-HPLC with UV detection at 220 nm.

According to a preferred embodiment, the composition GC does not contain the above mentioned glucagon deletion variants at a total concentration above 0.25%, 0.20%, 0.15%, 0.1%, 0.05%, or 0.01%, determined as the relative peak area observed in analytical RP-HPLC with UV detection at 220 nm.

A further aspect of the present invention relates to a composition GC comprising a glucagon peptide obtainable from a method according to any embodiment of the present invention, characterized in that said composition contains the glucagon peptide at a purity above 99.0%, determined as the relative peak area observed in analytical RP-HPLC with UV detection at 220 nm, and does not contain more than 0.3%, determined as the relative peak area observed in analytical RP-HPLC with UV detection at 220 nm, of any single glucagon derivative, glucagon truncation variant, derivative of a glucagon truncation variant, glucagon deletion variant, or derivative of a glucagon deletion variant.

A further aspect of the present invention relates to a composition GC comprising a glucagon peptide obtainable from a method according to any embodiment of the present invention, characterized in that said composition contains the glucagon peptide at a purity above 99.0%, determined as the relative peak area observed in analytical RP-HPLC with UV detection at 220 nm, and does contain detectable levels, but not more than 0.5%, determined as the relative peak area observed in analytical RP-HPLC with UV detection at 220 nm, of any single glucagon derivative, glucagon truncation variant, derivative of a glucagon truncation variant, glucagon deletion variant, or derivative of a glucagon deletion variant.

Therefore, a further aspect of the present invention relates to a composition GC comprising a glucagon peptide obtainable from a method according to any embodiment of the present invention, characterized in that said composition contains the glucagon peptide at a purity above 99.0% (w/w), referred to the summed mass of all peptide components, and does not contain more than 0.5% (w/w), referred to the summed mass of all peptide components, of any single glucagon derivative, glucagon truncation variant, derivative of a glucagon truncation variant, glucagon deletion variant, or derivative of a glucagon deletion variant.

Preferably, the composition GC contains glucagon at a purity above 99.1% (w/w), above 99.2% (w/w), above 99.3% (w/w), above 99.4% (w/w), above 99.5% (w/w), above 99.6% (w/w), above 99.7% (w/w), above 99.8% (w/w) or above 99.9% (w/w), referred to the summed mass of all peptide components.

According to a preferred embodiment, the composition GC does not contain the above mentioned glucagon deletion variants at a total concentration above 0.25% (w/w), 0.20% (w/w), 0.15% (w/w), 0.1% (w/w), 0.05% (w/w), or 0.01% (w/w), referred to the summed mass of all peptide components.

A further aspect of the present invention relates to a composition GC comprising a glucagon peptide obtained from a method according to the present invention, characterized in that said composition contains a glucagon peptide at a purity above 99.0%, and does contain detectable levels, but not more than 0.5%, preferably not more than 0.3%, in particular not more than 0.2%, and optionally even not more than 0.1% of Trp(O)$^{25}$-glucagon and/or of Glu$^{24}$-glucagon, des-Ser$^2$-glucagon, and/or des-Thr$^5$-glucagon.

A further aspect of the present invention relates to a composition GC comprising a glucagon peptide obtained from a method according to the present invention, characterized in that said composition contains a glucagon peptide at a purity above 99.0%, and contains 0.05-0.5%, preferably 0.05-0.3%, in particular 0.05-0.2%, and optionally only 0.05-0.1% of Trp(O)$^{25}$-glucagon and/or of Glu$^{24}$-glucagon, and/or des-Ser$^2$-glucagon, and/or des-Thr$^5$-glucagon.

One aspect of the present invention relates to a composition GC comprising a glucagon peptide obtained from a method according to the present invention, characterized in that said composition contains a glucagon peptide at a purity above 99.0%, and contains 0.05-0.5%, preferably 0.05-0.3%, in particular 0.05-0.2%, and optionally only 0.05-0.1% of Trp(O)$^{25}$-glucagon.

One aspect of the present invention relates to a composition GC comprising a glucagon peptide obtained from a method according to the present invention, characterized in that said composition contains a glucagon peptide at a purity above 99.0%, and contains 0.05-0.5%, preferably 0.05-0.3%, in particular 0.05-0.2%, and optionally only 0.05-0.1% of Glu$^{24}$-glucagon.

One aspect of the present invention relates to a composition GC comprising a glucagon peptide obtained from a method according to the present invention, characterized in that said composition contains a glucagon peptide at a purity above 99.0%, and contains 0.05-0.5%, preferably 0.05-0.3%, in particular 0.05-0.2%, and optionally only 0.05-0.1% of des-Ser$^2$-glucagon.

One aspect of the present invention relates to a composition GC comprising a glucagon peptide obtained from a method according to the present invention, characterized in that said composition contains a glucagon peptide at a purity above 99.0%, and contains 0.05-0.5%, preferably 0.05-0.3%, in particular 0.05-0.2%, and optionally only 0.05-0.1% of des-Thr$^5$-glucagon.

Preferably, the above percentages are determined as the relative peak area observed in analytical RP-HPLC with UV detection at 220 nm. Alternatively, the above percentages may be referred to the summed mass of all peptide components.

One aspect of the present invention relates to a composition GC comprising a glucagon peptide obtained from a method according to the present invention, characterized in that said composition contains a glucagon peptide at a purity above 99.0%, and does contain detectable levels, but not more than 0.5%, preferably not more than 0.3%, and particularly preferably not more than 0.2% of Glu$^{24}$-glucagon, and/or des-Ser$^2$-glucagon, and/or des-Thr$^5$-glucagon, wherein said concentrations are determined as the relative peak area observed in analytical RP-HPLC with UV detection at 220 nm.

One aspect of the present invention relates to a composition GC comprising a glucagon peptide obtained from a method according to the present invention, characterized in that said composition contains a glucagon peptide at a purity above 99.3%, and does contain detectable levels, but not more than 0.5%, preferably not more than 0.3%, and particularly preferably not more than 0.2% of Glu$^{24}$-glucagon, and/or des-Ser$^2$-glucagon, and/or des-Thr$^5$-glucagon, wherein said concentrations are determined as the relative peak area observed in analytical RP-HPLC with UV detection at 220 nm.

Preferably, all glucagon in the composition GC is obtained from a method according to the present invention.

The following Figures and Examples, including the experiments conducted and the results achieved, are provided for illustrative purposes only and are not to be construed as limiting the scope of the claims.

EXAMPLES

Example 1: Full Chemical Synthesis of Glucagon

A glucagon peptide according to SEQ ID NO: 1 was synthesized on a Wang resin using Fmoc-protected amino acid derivatives and optionally two pseudoproline dipeptide derivatives. For each chain elongation cycle, the coupling reagent mixture comprised TBTU plus DIPEA, DIC plus Oxyma, or DEPBT plus DIPEA. After synthesis, the peptide chain was cleaved from the resin and de-protected by incubation with concentrated TFA in the presence of scavengers under inert gas. Ammonium iodide was added to the cleavage mixture and the formed iodine was subsequently reduced by addition of ascorbic acid. Resin and cleavage solution were separated by filtration and the crude peptide was precipitated from the cleavage solution using diisopropyl ether (IPE) as anti-solvent. The dried peptide precipitate was redissolved in aqueous acetic acid and decarboxylated to yield a crude peptide solution with a glucagon content of around 40 to 80%.

Figure 1:
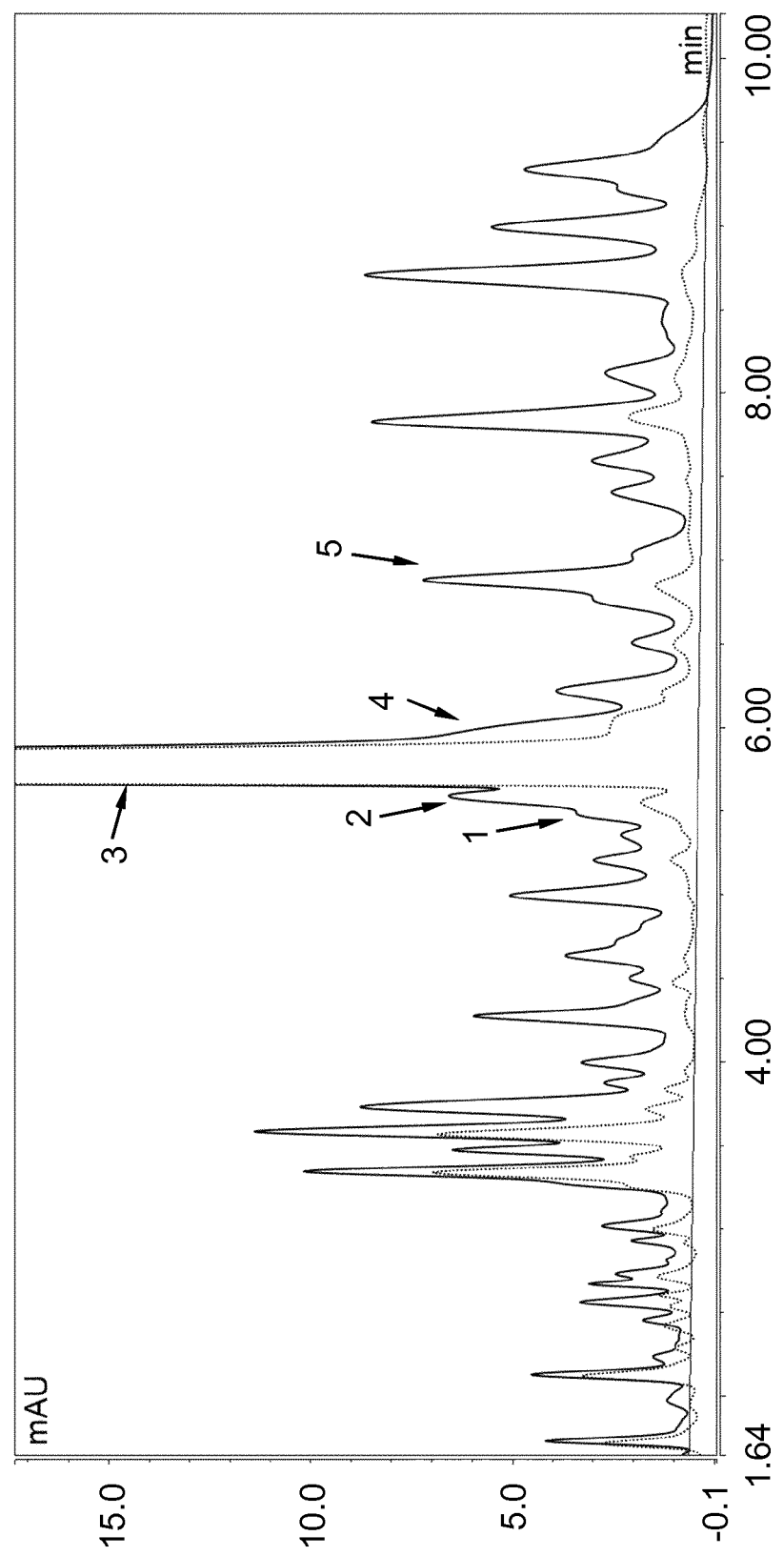
FIG. 1 shows analytical RP-UHPLC traces of crude glucagon peptide solutions prepared without (black) and with (grey) the use of pseudoproline dipeptides. Absorbance at 220 nm in mAU is plotted vs. retention time in min. Des-Thr5-, des-Ser2-, and Glu24-glucagon were identified as significant impurities in both cases, based on co-elution with independently synthesized reference compounds and prior LC-MS analysis.

Crude glucagon peptide solutions prepared without (black line) and with (grey line) the use of pseudoproline dipeptides were analyzed by UHPLC (cf. FIG. 1). Des-Thr$^5$-, des-Ser$^2$-, and Glu$^{24}$-glucagon were identified as significant impurities in both cases, based on relative retention times, spiking experiments, and prior LC-MS analysis. Moreover, an impurity with RRT 1.042, which is likely to correspond to Glu$^3$-glucagon, was observed. The concentrations of these related substances are given in area percent of the total peak area in table 2 below.

TABLE 2

| Peak Number | Related substance | Synthesis without pseudoproline dipeptides | Synthesis with pseudoproline dipeptides |
|---|---|---|---|
| 1 | des-Thr5 glucagon | 0.49 | 0.27 |
| 2 | des-Ser2 glucagon | 1.67 | 0.54 |
| 5 | Glu24 glucagon | 2.54 | 0.61 |
| 4 | RRT 1.042 | 1.56 | 1.40 |

The data demonstrate that the use of two pseudoproline dipeptide building blocks during SPPS allows to improve the direct product of solid phase peptide synthesis, i.e. the solid phase conjugated glucagon peptide, to a surprising extent. The resulting solid phase conjugated glucagon peptide is characterized by a considerable reduction of unwanted substances in general (purity of crude glucagon was 56.21 vs. 82.43 percent) and in particular by a reduction of des-Thr$^5$-, des-Ser$^2$-, and Glu$^{24}$-glucagon.

Example 2: Pre-Purification

Especially if the glucagon content of the material prepared according to Example 1 is below 80%, it is recommended to perform a pre-purification step. Buffer A (0.1% aqueous TFA) and Buffer B (0.1% TFA in 60% aqueous acetonitrile) were prepared. A crude peptide solution prepared as in Example 1 was loaded on a reversed-phase chromatography column (C18 silica) pre-equilibrated with Buffer A, the column was flushed with 1.2 column volumes (CV) of Buffer A and eluted with a linear gradient of 20% to 100% Buffer B, while monitoring peptide elution with a UV-detector at 220 nm. Glucagon-containing fractions were pooled to yield a pre-purified glucagon preparation. This preparation may be lyophilized. The overall purity of the product thus obtained was (purity: 94.27%).

Figure 2:
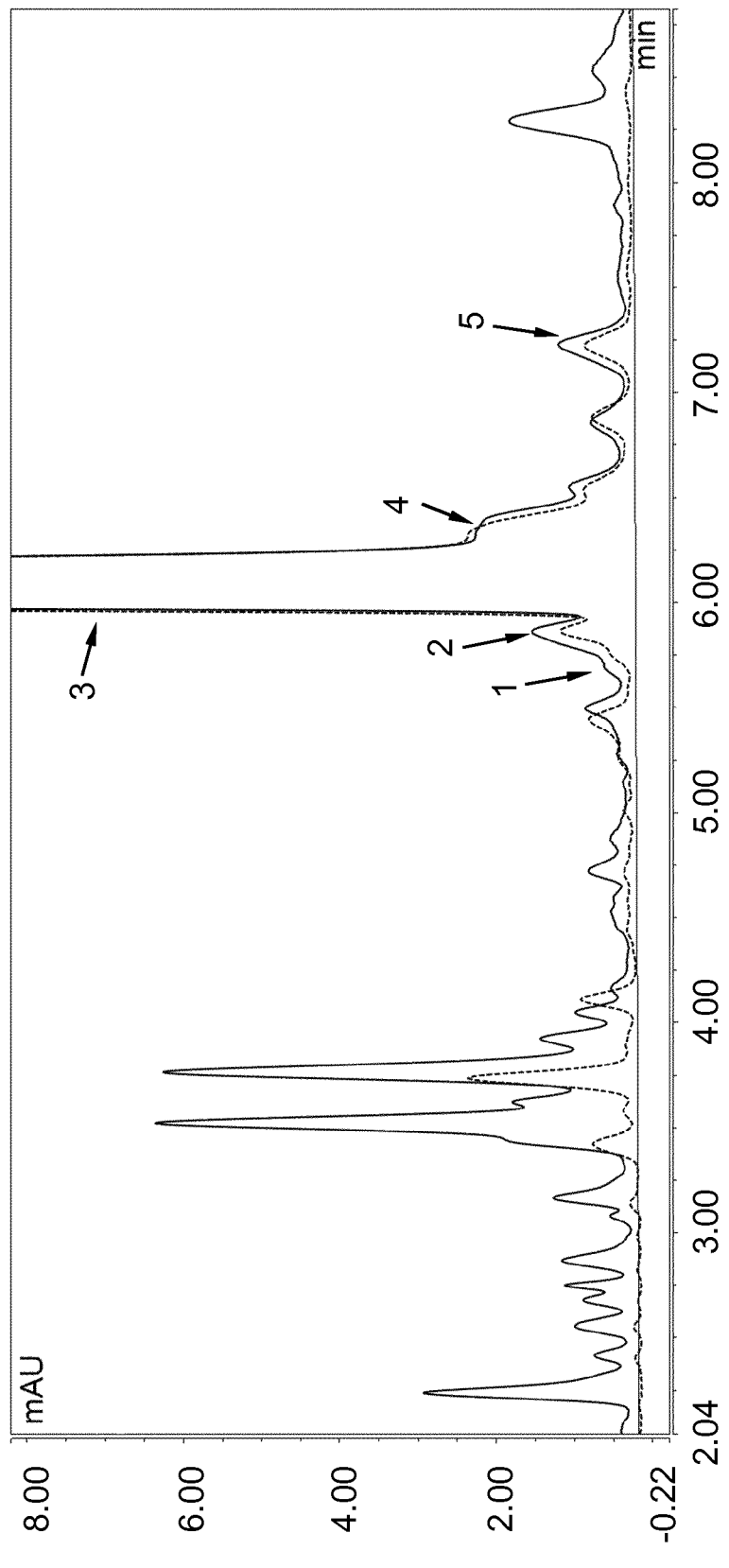
FIG. 2 shows analytical RP-UHPLC traces of a crude glucagon preparation (solid line) and of a corresponding pre-purified glucagon preparation (dotted). Absorbance at 220 nm in mAU is plotted vs. retention time in min. Des-Thr5-, des-Ser2-, and Glu24-glucagon were identified as significant impurities in both cases, based on relative retention times and prior LC-MS analysis. It can be seen that removal of these impurities is not satisfactory in the pre-purification step.

FIG. 2 shows analytical RP-UHPLC traces of a pure crude glucagon preparation (solid line) and of the pre-purified glucagon preparation (dotted). It can be seen that, while the overall purity of the preparation increased, the relative content of des-Ser2-, and Glu3-glucagon not reduced at all, and that the content in des-Thr5- and Glu24-glucagon was unsatisfactory high. One of the challenges in developing a powerful purification protocol is therefore to separate these impurities from the desired glucagon sequence despite their similarity.

Example 3: Two Dimensional RP-HPLC Purification

A glucagon preparation obtained as in example 2 was subjected to a two-dimensional purification using C18 bonded silica. The same column was used for both purification steps and peptide elution was monitored by following UV absorption.

A pre-purified glucagon preparation (purity: 95.48%) was loaded on a reversed-phase chromatography column (C18 silica, 10 μm particles with a pore size of 100 Å), and the peptide was eluted as indicated in table 3 below. Purified glucagon-containing fractions were pooled to yield an intermediate glucagon preparation.

TABLE 3

Parameters TEAP purification dimension
Buffer A 19 mM aqueous triethylammonium phosphate pH 7.0
Buffer B 60% (v/v) acetonitrile in Buffer A
Elution protocol

| Total Buffer Volume [CV] | Buffer A [%] | Buffer B [%] |
|---|---|---|
| 0 | 95 | 5 |
| 0.5 | 95 | 5 |
| 0.5 | 95 | 5 |
| 1.9 | 58 | 42 |
| 1.9 | 58 | 42 |
| 13.5 | 33 | 67 |

The intermediate glucagon preparation was further purified as indicated in table 4 below on a reversed-phase chromatography column (C18 silica, 10 μm particles with a pore size of 100 Å).

TABLE 4

Buffer A 350 mM acetic acid
Buffer B 60% (v/v) acetonitrile in Buffer A
Elution protocol

| Total Buffer Volume [CV] | Buffer A [%] | Buffer B [%] |
|---|---|---|
| 0 | 95 | 5 |
| 0.5 | 95 | 5 |
| 0.5 | 95 | 5 |
| 1.9 | 70 | 30 |
| 1.9 | 70 | 30 |
| 6.5 | 20 | 80 |

Figure 3:
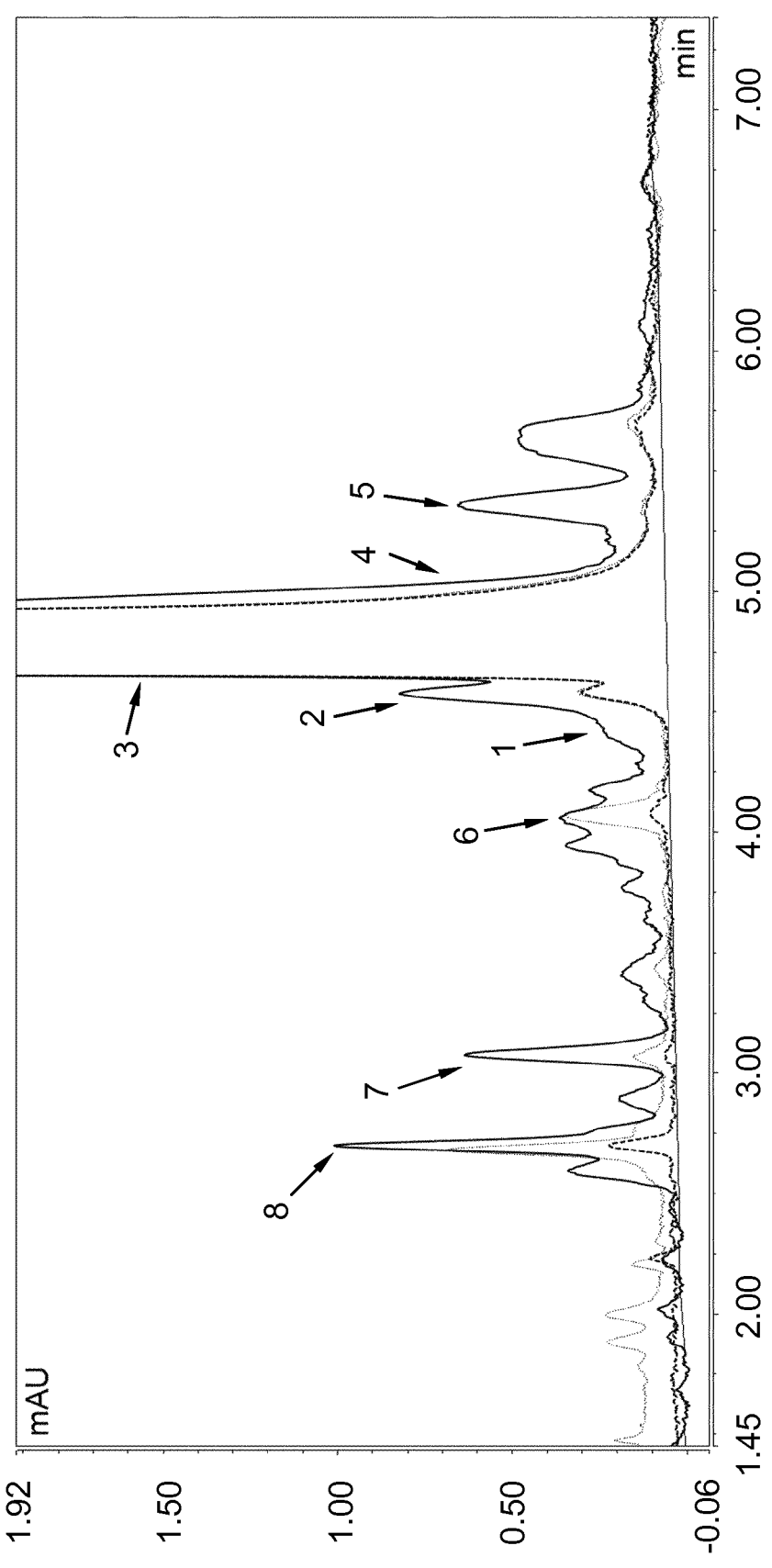
FIG. 3 shows analytical RP-HPLC traces of a pre-purified glucagon preparation (black), an intermediate glucagon preparation obtained from pooling purified glucagon-containing fractions after the first (TEAP) purification dimension as described in example 3 (grey), and a highly pure glucagon preparation obtained from pooling glucagon-containing fractions after the second (acetic acid) purification dimension as described in example 3 (asterisks). It can be seen that both dimensions are complementary to each other regarding the removal of the related substances and result in excellent product purity.

The purity of the pooled fractions after the second purification dimension was 99.42% as assessed by analytical RP-UHPLC, the overall yield after both steps was 57.3%. No single unwanted component could be detected at a concentration above 0.5%. Comparison of the analytical RP-UHPLC traces of starting material and of the pooled fractions after the first and second HPLC pass demonstrated the surprising complementarity of both purification dimensions: Each purification dimension removed different unwanted components, such that the combination of both steps resulted in excellent product purity (cf. FIG. 3). Table 5 details the removal of specific dominant impurities.

TABLE 5

| Peak Number | Related substance | Feed TEAP dimension | Feed AcOH dimension | Pool AcOH dimension |
|---|---|---|---|---|
| 1 | des-Thr5 glucagon | 0.13 | <LOD | <LOD |
| 2 | des-Ser2 glucagon | 0.48 | 0.11 | 0.11 |
| 3 | glucagon | 95.48 | 98.67 | 99.42 |
| 4 | RRT 1.05 | 0.64 | 0.45 | 0.18 |
| 5 | Glu24 glucagon | 0.24 | 0.13 | 0.11 |
| 6 | RRT 0.86 | 0.22 | 0.18 | <LOD |
| 7 | RRT 0.65 | 0.28 | <LOD | <LOD |
| 8 | RRT 0.57 | 0.37 | 0.22 | 0.06 |

Sequence listing

SEQ ID NO: 1 human glucagon
HSQGTFTSDYSKYLDSRRAQDFVQWLMNT

SEQ ID NO: 2 human des-Thr5-glucagon
HSQGFTSDYSKYLDSRRAQDFVQWLMNT

SEQ ID NO: 3 human des-Ser2-glucagon
HQGTFTSDYSKYLDSRRAQDFVQWLMNT

SEQ ID NO: 4 human Glu24-glucagon
HSQGTFTSDYSKYLDSRRAQDFVEWLMNT

The invention claimed is:

1. A method for the preparation of purified glucagon peptide, comprising:

a) providing a liquid composition C comprising a chemically synthesized glucagon peptide and at least one peptidic impurity selected from a glucagon derivative, a glucagon truncation variant, a derivative of a glucagon truncation variant, a glucagon deletion variant, a derivative of a glucagon deletion variant, and a combination thereof;

b) subjecting the composition C to a first reversed phase high performance liquid chromatography (RP-HPLC) purification, wherein a hydrocarbon bonded silica is used as a stationary phase, an aqueous mobile phase of pH 6.5 to 7.5 comprising triethylammonium phosphate and acetonitrile is used, and elution is effected by gradually increasing the acetonitrile concentration within the mobile phase while collecting fractions containing the glucagon peptide; and c) subjecting the pooled glucagon peptide-containing fractions obtained in step b) to a second reversed phase HPLC purification, wherein a hydrocarbon bonded silica is used as a stationary phase, a mobile phase comprising acetic acid and acetonitrile is used, wherein the concentration of acetic acid in the mobile phase of step c) is between 0.5 and 5% v/v, and elution is effected by gradually increasing the acetonitrile concentration within the mobile phase while collecting and pooling fractions containing the purified glucagon peptide, wherein the same stationary phase is used in steps b) and c).

2. The method according to claim 1, wherein elution in step b) is effected by a gradient of increasing the acetonitrile content from 2 to 4% v/v acetonitrile to 30 to 50% v/v acetonitrile, and wherein elution in step c) is effected by a gradient of increasing the acetonitrile content from 2 to 4% v/v acetonitrile to 40 to 60% v/v acetonitrile.

3. The method according to claim 1, wherein C18 bonded silica is used as a stationary phase in step b) and step c).

4. The method according to claim 1, further comprising a step of rinsing the stationary phase with an aqueous solution comprising TFA and acetonitrile prior to loading with the liquid composition C, prior to loading with the pooled glucagon peptide containing fractions obtained in step b), or prior to loading with the liquid composition C and prior to loading with the pooled glucagon peptide containing fractions obtained in step b).

5. The method according to claim 1, further comprising the step of:

d) performing an anion exchange.

6. The method according to claim 1, wherein step a) comprises:

(a-i) providing a glucagon peptide conjugated to a solid phase, wherein at least the side chains of Glu, Asp, and Lys carry protecting groups; and (a-ii) cleaving the glucagon peptide from the solid phase and removing the protection groups from the glucagon peptide.

7. The method according to claim 6, wherein the glucagon peptide conjugated to a solid phase comprises two pseudo-proline dipeptides.

8. The method according to claim 6, wherein step (a-i) comprises performing Fmoc-based Solid Phase Peptide Synthesis of a glucagon peptide using suitably protected amino acid derivatives or dipeptide derivatives, wherein said protected amino acid derivatives or dipeptide derivatives are activated by means of one or more coupling reagent mixtures comprising reagents selected for each step independently from the group consisting of:

(E) (benzotriazolyl)tetramethyluronium tetrafluoroborate (TBTU) plus diisopropylethylamine (DIPEA);

(F) diisopropylcarbodiimide (DIC) plus cyano-hydroxy-imino-acetic acid ethyl ester (Oxyma);

(G) 3-(diethoxy-phosphoryloxy)-3H-benzo[d][1,2,3]triazin-4-one (DEPBT) plus DIPEA; and (H) DIC plus hydroxybenzotriazole (HOBt).

9. The method according to claim 6, wherein an N-terminal histidine moiety is introduced into the glucagon peptide conjugated to the solid phase using an amino acid derivative selected from the group consisting of Boc-His (Boc)-OH, Boc-His(Trt)-OH, and Fmoc-His(Trt)-OH and a coupling reagent mixture comprising DEPBT plus DIPEA or DIC plus Oxyma.

10. The method according to claim 1, wherein the glucagon peptide is a peptide of SEQ ID NO: 1.

11. The method according to claim 1, wherein step a) comprises subjecting a sample comprising a glucagon peptide to a reversed phase high performance liquid chromatography (RP-HPLC) purification, wherein a hydrocarbon bonded silica is used as a stationary phase, an aqueous mobile phase comprising trifluoroacetic acid and acetonitrile is used, and elution is effected by gradually increasing the acetonitrile concentration within the mobile phase while collecting fractions containing the glucagon peptide.

12. The method according to claim 6, wherein the step of cleaving the glucagon peptide from the solid phase and removing the protection groups from the glucagon peptide is achieved by incubation with a cleavage composition comprising at least 50% TFA and one or more scavenger(s).

13. A composition GC comprising a glucagon peptide obtained from a method according to claim 1, characterized in that said composition contains a glucagon peptide at a purity above 99.3%, and does contain detectable levels, but not more than 0.5% of one or more selected from the groups consisting of $Glu^{24}$-glucagon, des-$Ser^2$-glucagon, and des- Thr$^5$-glucagon, wherein said concentrations are determined as the relative peak area observed in analytical RP-HPLC with UV detection at 220 nm.

14. The method according to claim 1, further comprising the step of:

d) Performing an anion exchange, wherein acetate is at least partially replaced by chloride, wherein the anion exchange is achieved by lyophilization, ultrafiltration, dialysis, solid phase extraction, reversed-phase chromatography or by ion exchange chromatography, or wherein acetate is at least partially replaced by chloride and wherein the anion exchange is achieved by lyophilization, ultrafiltration, dialysis, solid phase extraction, reversed-phase chromatography or by ion exchange chromatography.

15. The method according to claim 6, wherein the glucagon peptide conjugated to a solid phase comprises two pseudoproline dipeptides, wherein the two pseudoproline dipeptides are introduced at positions corresponding to or identical with the positions selected from the group consisting of: Gly$^4$-Thr$^5$ and Phe$^6$-Thr$^7$, Gly$^4$-Thr$^5$ and Thr$^7$-Ser$^8$, Gly$^4$-Thr$^5$ and Tyr$^{10}$-Ser$^{11}$, Gly$^4$-Thr$^5$ and Asp$^{15}$-Ser$^{16}$, Phe$^6$-Thr$^7$ and Tyr$^{10}$-Ser$^{11}$, Phe$^6$-Thr$^7$ and Asp$^{15}$-Ser$^{16}$, Thr$^7$-Ser$^8$ and Tyr$^{10}$-Ser$^{11}$, Thr$^7$-Ser$^8$ and Asp$^{15}$-Ser$^{16}$, or Tyr$^{10}$-Ser$^{11}$ and Asp$^{15}$-Ser$^{16}$ of the peptide of SEQ ID NO: 1.

16. The method according to claim 6, wherein one or more agents selected from the group consisting of iodide salts, dimethyl sulfide, 1,4-dithiothreitol, trimethylsilylbromide, and ascorbic acid is or are added to a suspension comprising the solid phase.

17. The composition GC according to claim 13, characterized in that said composition does contain detectable levels, but not more than 0.3% of one or more selected from the groups consisting of Glu24-glucagon, des-Ser$^2$-glucagon, and des-Thr$^5$-glucagon, wherein said concentrations are determined as the relative peak area observed in analytical RP-HPLC with UV detection at 220 nm.

18. The composition GC according to claim 13, characterized in that said composition does contain detectable levels, but not more than 0.2% of one or more selected from the groups consisting of Glu24-glucagon, des-Ser$^2$-glucagon, and des-Thr$^5$-glucagon, wherein said concentrations are determined as the relative peak area observed in analytical RP-HPLC with UV detection at 220 nm.

19. The method of claim 1, wherein the at least one peptidic impurity results from omission or addition of at least one amino acid during glucagon peptide synthesis.

20. The method of claim 1, wherein the at least one peptidic impurity results from incomplete removal of protecting groups, from side reactions occurring during peptide cleavage from a solid support, from racemization, and/or from deamidation.

21. The method of claim 1, wherein the collected and pooled glucagon peptide comprises no more than 0.5% of any individual peptidic impurity as assessed by UV detection at a wavelength between 205 and 230 nm.

* * * * *